United States Patent [19]

Shepard

[11] Patent Number: 5,704,371
[45] Date of Patent: Jan. 6, 1998

[54] MEDICAL HISTORY DOCUMENTATION SYSTEM AND METHOD

[76] Inventor: Franziska Shepard, 1414 E. Main St., Santa Maria, Calif. 93454

[21] Appl. No.: 611,642

[22] Filed: Mar. 6, 1996

[51] Int. Cl.⁶ .................................................. G06F 15/42
[52] U.S. Cl. ................................................................ 128/897
[58] Field of Search .................................. 128/710, 897; 364/413.02, 413.04, 413.14, 419.14

[56] References Cited

U.S. PATENT DOCUMENTS 4,991,091  2/1991  Allen ............................. 364/413.02
5,267,155  11/1993  Buchanan et al. ............... 364/419.14

Primary Examiner—Scott Getzow
Attorney, Agent, or Firm—Daniel J. Meaney, Jr.

[57] ABSTRACT

A medical history documentation system and method for recording information relating to at least one of a designated patient's current medical condition, a physical examination, a diagnosis and a treatment plan is shown. The system includes a recording member having a plurality of discrete recording sections formed thereon programmed for recording information relating to the patient. The encoded indicia is communicated by a first person to a second person during a physical examination of the patient by the first person. An input member is used by the second person for recording medical information in the form of predetermined encoded indicia in applicable discrete recording sections of the recording member. A transcriber having a plurality of report section templates is used. Each report section template corresponds to a discrete recording section. Each of the report section templates comprise a plurality of optional text variable segments each of which are assigned to a selected one of the predetermined encoded indicia. The transcriber is operative to decode each one of the predetermined encoded indicia recorded on the recording member. An imaging device responsive to the transcriber prepares a patient's report specific to the designated patient. A method for using the system is shown.

33 Claims, 21 Drawing Sheets

PATIENT INFORMATION SHEET (NEW W/C RETURN POST-OP OSTEO)

SURGERY: Type: _____ Date: _____

Last Name: _____
First Name: _____
Race: O  SP-C  C  N                    Male    Female
Job Description: _____
Requires: Bending  Stooping  Twisting  Reaching  Standing  Walking
          Working overhead  Lifting  Sitting  Kneeling
ALLERGIES: NKA

CURRENT MEDICATIONS: NONE

SHOULD THIS REPORT BE IN LETTER STYLE?   yes   no
If yes, where should additional letter be sent?
Attorney _____ Referring Physician _____ Other _____

Which body part(s) are injured?
Cervical spine, Shoulder, Elbow, Wrist, Hand, Fingers,
Thoracic spine, Lumbar spine, Hip, Knee, Ankle, Foot, Toe Date of last visit: _____
Prior Tests and results: _____
Medication since last visit: _____
Physical Therapy since last visit: _____
Does the patient have pain which awakens them at night?   yes   no
If yes, number of times: _____

ACTIVITY RECORD (W/C ONLY)
Patient can do the following:   Lift _____ lbs
Sit for   _____ hrs _____ min    Kneel   N   O   F
Stand for _____ hrs _____ min    Climb   N   O   F
Walk for  _____ hrs _____ min    Bend    N   O   F
Ride in Car _____ hrs _____ min  Twist   N   O   F R  L  RL
PAIN DESCRIPTION:
Pain Description: Throbbing, Stabbing  Burning  Dull/Aching
Sharp
Radiation (Cervical and Lumbar): Shoulder R/L  Arm R/L  Hand R/L
Buttock R/L  Thigh R/L  Calf R/L  Foot R/L
Pain is made worse with cough or sneeze?   yes   no
Loss of control of bowel or bladder?   yes   no
Other symptoms: Inability to bear weight, Popping, Stiffness,
Swelling, Cramping, Heaviness, Numbness, Tingling, Soreness
Change since last visit: Improved  Unchanged  Worse
Has had this pain before?   yes   no   multiple times  once years ago
Pain made worse by: Sitting, Standing, Walking, Riding in a car
Lifting, Twisting, Working overhead, Bending
Pain improved by: Rest  Heat  Ice  Medication  Physical therapy
Chiropractic treatments  Home exercise program

R  L  RL
PAIN DESCRIPTION:
Pain description: Throbbing  Stabbing  Burning  Dull/Aching
Radiation (Cervical and Lumbar): Shoulder R/L  Arm R/L  Hand R/L
Buttock R/L  Thigh R/L  Calf R/L  Foot R/L
Pain is made worse with cough or sneeze?   yes   no
Loss of control of bowel or bladder?   yes   no
Other symptoms: Inability to bear weight, Popping, Stiffness,
Swelling, Cramping, Heaviness, Numbness, Tingling, Soreness
Change since last visit: Improved  Unchanged  Worse
Has had this pain before?   yes   no   multiple times  once years ago
Pain made worse by: Sitting, Standing, Walking, Riding in a car
Lifting, Twisting, Working overhead, Bending
Pain improved by: Rest  Heat  Ice  Medication  Physical therapy
Chiropractic treatments  Home exercise program R  L  RL
PAIN DESCRIPTION:
Pain description: Throbbing  Stabbing  Burning  Dull/Aching
Sharp
Radiation (Cervical and Lumbar): Shoulder R/L  Arm R/L  Hand R/L
Buttock R/L  Thigh R/L  Calf R/L  Foot R/L
Pain is made worse with cough or sneeze?   yes   no
Loss of control of bowel or bladder?   yes   no
Other symptoms: Inability to bear weight, Popping, Stiffness,
Swelling, Cramping, Heaviness, Numbness, Tingling, Soreness
Change since last visit: Improved  Unchanged  Worse
Has had this pain before?   yes   no   multiple times  once years ago
Pain made worse by: Sitting, Standing, Walking, Riding in a car
Lifting, Twisting, Working overhead, Bending
Pain improved by: Rest  Heat  Ice  Medication  Physical therapy
Chiropractic treatments  Home exercise program PHYSICAL EXAMINATION
Cervical spine              Lumbar spine            Pulses Lower
Shoulder                    Thoracic spine          Osteo 1
Elbow                       Hips                    Osteo 2
Wrist                       Knees                   Osteo 3
Hand                        Ankles and feet
Thumb                       Great toe
Index finger                Second
Long finger                 Third
Ring finger                 Fourth
Fifth finger                Fifth
Strength upper              Straight leg raising
Reflex upper                Measurements lower
Measurements upper          Strength lower
Pulses upper                Reflex lower
Jaymar

Fig. 13 (304):

Areas of tenderness:
Areas of erythema:
Areas of swelling:
Areas of ecchymosis:

GENERAL APPEARANCE:
Cervical lordosis: present/absent
Muscle spasm: present/absent  location _____
Contusions: present/absent
Scars: present/absent  location _____

RANGE OF MOTION OF THE CERVICAL SPINE:

|  | RIGHT | LEFT |
|---|---|---|
| Flexion: | 0-20 |  |
| Extension: | 0-20 |  |
| Rotation (R): | 0-90 |  |
| Rotation (L): | 0-90 |  |
| Lateral bend (R): | 0-20 |  |
| Lateral bend (L): | 0-20 |  |

SHOULDERS:

|  | RIGHT | LEFT |
|---|---|---|
| Flexion: | 0-180 | 0-180 |
| Extension: | 0-20 | 0-20 |
| Abduction: | 0-180 | 0-180 |
| Adduction: | 0-90 | 0-90 |
| Internal rotation: | 0-90 | 0-90 |
| External rotation: | 0-90 | 0-90 |
| Crepitation: | neg | neg |
| Thumb to |  | in extension |

ELBOWS:

|  | RIGHT | LEFT |
|---|---|---|
| Flexion/Extension: | 0-135 | 0-135 |
| Supination: | 0-90 | 0-90 |
| Pronation: | 0-90 | 0-90 |
| Pain on extension of wrist | no | no |
| Pain on flexion of wrist | no | no |

WRISTS AND HANDS:

|  | RIGHT | LEFT |
|---|---|---|
| Flexion: | 0-90 | 0-90 |
| Extension: | 0-90 | 0-90 |
| Ulnar deviation: | 0-35 | 0-35 |
| Radial deviation: | 0-15 | 0-15 |
| Tinel's (cts): | neg | neg |
| Finkelstein's: | neg | neg |
| Phalen's (cts): | neg | neg |
| O test: | neg | neg |
| Thenar atrophy (cts) | neg | neg |
| Hypothenar atrophy (cts) | neg | neg |
| Crepitation: | neg | neg |
| Palpable spurs: | no | no |
| Ganglions: |  |  |
| volar | no | no |
| dorsal | no | no |

Fig. 14 (306):

THUMB AND FINGERS:

|  | RIGHT | LEFT |
|---|---|---|
| M.P. | 0-90 | 0-90 |
| Crepitation: | neg | neg |
| Palpable spurs: | neg | neg |
| Instability: | neg | neg |
| P.I.P. | 0-90 | 0-90 |
| Crepitation: | neg | neg |
| Palpable spurs: | neg | neg |
| Instability: | neg | neg |
| D.I.P. | 0-90 | 0-90 |
| Crepitation: | neg | neg |
| Palpable spurs: | neg | neg |
| Instability: | neg | neg |
| Trigger finger: | neg | neg |

MUSCLE STRENGTH DETERMINATION:

|  | RIGHT | LEFT |
|---|---|---|
| Deltoid - Ant. | 5/5 | 5/5 |
| Med. | 5/5 | 5/5 |
| Shoulder Int. rotation: | 5/5 | 5/5 |
| Shoulder Ext. rotation: | 5/5 | 5/5 |
| Biceps: | 5/5 | 5/5 |
| Triceps: | 5/5 | 5/5 |
| Brachial radialis: | 5/5 | 5/5 |
| Wrist flexors: | 5/5 | 5/5 |
| Finger flexors: | 5/5 | 5/5 |
| Finger extensors: | 5/5 | 5/5 |
| Intrinsics: | 5/5 | 5/5 |

JAMAR Grip strength: / /
Lateral pinch: / /
Chuck pinch: / /

REFLEX REACTION:

|  | RIGHT | LEFT |
|---|---|---|
| Biceps: | 2+ | 2+ |
| Triceps: | 2+ | 2+ |
| Pectoral: | 2+ | 2+ |
| Brachial radialis: |  |  |

SENSATION: normal / normal

PULSES:

|  | RIGHT | LEFT |
|---|---|---|
| Radial: | 2+ | 2+ |
| Ulnar: | 2+ | 2+ |
| Maintained with shoulder abduction: | yes | yes |

MEASUREMENTS:

|  | RIGHT | LEFT |
|---|---|---|
| Upper arm (5" above the olecranon): |  |  |
| Lower arm (5" below the olecranon): |  |  |

Fig. 15 (308)

| | |
|---|---|
| Areas of tenderness: | yes/no |
| Areas of erythema: | present/absent |
| Areas of swelling: | present/absent |
| Areas of ecchymosis: | present/absent |

GENERAL APPEARANCE:

| | |
|---|---|
| Shoulder and Pelvis level: | present/absent |
| Lumbar lordosis: | yes/no |
| Scoliosis: | |
| Muscle spasms: | |
| Contusions: | |
| Scars: | |
| Toes/Heels: | yes/no |
| Squat and stand: | _____ " from floor |

RANGE OF MOTION OF THE LUMBAR SPINE:

| | RIGHT | LEFT |
|---|---|---|
| Flexion: | 0-90 | 0-90 |
| Extension: | 0-30 | 0-30 |
| Left lateral bend: | 0-30 | 0-30 |
| Right lateral bend: | 0-30 | 0-30 |
| Left rotation: | 0-90 | 0-90 |
| Right rotation: | 0-90 | 0-90 |

STRAIGHT LEG RAISING:

| | RIGHT | LEFT |
|---|---|---|
| Supine: | 90 degrees | 90 degrees |
| Sitting: | 90 degrees | 90 degrees |
| Lasegues: | negative | negative |
| Hamstring tightening | 90 | 90 degrees |

HIP EXAMINATION:

| | RIGHT | LEFT |
|---|---|---|
| Flexion: | 0-130 | 0-130 |
| Extension: | 0-30 | 0-30 |
| Abduction: | 0-45 | 0-45 |
| Adduction: | 0-30 | 0-30 |
| Internal rotation: | 0-85 | 0-85 |
| External rotation: | 0-60 | 0-60 |
| Crepitation: | absent | absent |
| Trendelenburg: | negative | negative |

KNEE EXAMINATION:

| | RIGHT | LEFT |
|---|---|---|
| Flexion/Extension: | 0-135 | 0-135 |
| Effusion: | 0 | 0 |
| Anterior cruciate: | stable | stable |
| Posterior cruciate: | stable | stable |
| Medial collateral: | stable | stable |
| Lateral collateral: | stable | stable |
| McMurray's: | negative | negative |
| Lachman's: | negative | negative |
| Pivot shift: | negative | negative |
| Patellofemoral crepitation: | 0/4+ | 0/4+ |

Tenderness:

| | RIGHT | LEFT |
|---|---|---|
| Medial joint line: | 0/4+ | 0/4+ |
| Lateral joint line: | 0/4+ | 0/4+ |
| Peripatellar: | 0/4+ | 0/4+ |
| Strength: | | |
| Vastus medialis: | normal bulk | normal bulk |
| Palpable spurs: | no | no |

Fig. 16 (310)

ANKLES AND FEET:

| | RIGHT | LEFT |
|---|---|---|
| Dorsiflexion: | 0-20 | 0-20 |
| Plantar flexion: | 0-40 | 0-40 |
| Inversion: | 0-10 | 0-10 |
| Eversion: | 0-20 | 0-20 |
| Crepitation: | negative | negative |
| Palpable spurs: | no | no |
| Instability: | no | no |

TOES:

| | RIGHT | LEFT |
|---|---|---|
| M.P. | 0-90 | 0-90 |
| Crepitation: | no | no |
| Palpable spurs: | no | no |
| Instability: | no | no |
| P.I.P. | 0-90 | 0-90 |
| Crepitation: | no | no |
| Palpable spurs: | no | no |
| Instability: | no | no |
| D.I.P. | 0-90 | 0-90 |
| Crepitation: | no | no |
| Palpable spurs: | no | no |
| Instability: | no | no |

DEEP TENDON REFLEXES:

| | RIGHT | LEFT |
|---|---|---|
| Patellar: | 2+ | 2+ |
| Achilles: | 2+ | 2+ |

MUSCLE STRENGTH EVALUATION:

| | RIGHT | LEFT |
|---|---|---|
| Hip: | 5/5 | 5/5 |
| Flexion: | 5/5 | 5/5 |
| Extension: | 5/5 | 5/5 |
| Internal rotation: | 5/5 | 5/5 |
| External rotation: | 5/5 | 5/5 |
| Quadriceps: | 5/5 | 5/5 |
| Hamstrings: | 5/5 | 5/5 |
| Anterior tibialis: | 5/5 | 5/5 |
| Gastrocnemius: | 5/5 | 5/5 |
| Peroneals: | 5/5 | 5/5 |
| Extensor hallux: | 5/5 | 5/5 |
| Flexor hallux: | 5/5 | 5/5 |
| Extensor digitorum: | 5/5 | 5/5 |
| Flexor digitorum: | 5/5 | 5/5 |

SENSATION:

| | RIGHT | LEFT |
|---|---|---|
| | Normal | Normal |

PULSES:

| | RIGHT | LEFT |
|---|---|---|
| Dorsalis pedis: | 2+ | 2+ |
| Posterior tibial: | 2+ | 2+ |
| Popliteal: | 2+ | 2+ |
| Femoral: | 2+ | 2+ |

MEASUREMENTS:

| | RIGHT | LEFT |
|---|---|---|
| Thigh - 2" above patella | | |
| 4" above patella | | |
| 6" above patella | | |
| Calf (at maximum circumference: | | |
| Leg length: | | |

Fig. 17

LOCATION     X-RAY     # OF VIEWS (1-5)     N/A

_____

_____

_____

_____

A-Cervical spine  B-Thoracic spine  C-Lumber spine  D-Shoulders
E-Humerus  F-Elbow  G-Forearm  H-wrist  I-Hand  J-Thumb
K-Finger  L-Hip  M-Femur  N-Knee  O-Tibia  P-Ankle  Q-Foot

ABNORMAL: A B C

Cervical, Lumbar and Thoracic spine:
Alignment is normal/abnormal.
Paravertebral soft tissues are normal/abnormal.
Lordosis is normal/abnormal.
The intervertebral disc spaces are maintained/narrow.
Evidence of congenital:  yes/no
Evidence of degenerative:  yes/no
Evidence of post-traumatic abnormalities:  yes/no
Disrupted at _____

Other _____

OTHER:
The bony contours are normal/abnormal.
Consistency is normal/osteoporotic/abnormal.
The cortex is intact/disrupted.
Joint surfaces are: Normal  Irregular
Contour:  Normal  Narrowed
Height:  Normal  Narrowed
Spurs:   Present  Absent Other _____

FRACTURE:
1. The fracture alignment is satisfactory.
2. The fracture alignment is satisfactory with good callus.
3. Free bodies.
4. Retained surgical metal.

Fig. 18

DIAGNOSIS:

The patient was instructed in a home exercise program?  yes  no
PHYSICAL THERAPY:  Ordered  Continued  Changed  Discontinued  None
L-Lumbar program  C-Cervical Program  B-Back School  E-electrostim
I-Iontophoresis  Q-Quadriceps Program  R-Range of Motion
S-Strengthening  K-Knee  O-Other
_____ times for _____ weeks.     Surgery was discussed in detail, including complications, alternatives and
prognosis.
Scheduled at/for _____
Chiropractic care was discussed with patient:  Y/N
Medication prescribed: _____
Testing ordered: _____

Referral initiated or requested to _____
for _____

DISCUSSION:

CURRENT STATUS:
A. Working without limitations  B. Working with limitations
C. Not working  R. Retired  S. Student
K. Child  H. Housewife
If the patient is not working:
D. Released for work on _____ (date)
E. Estimated time before released for work. __ # __ W  M

DISABILITY STATUS:
A. Temporarily partially disabled with no expectation of
   permanent disability.
F. Temporarily partially disabled with expectation of some
   level of permanent disability.
B. Temporarily totally disabled.
C. Permanent and stationary with no disability.
D. Permanent and stationary with rateable disability.
E. Permanent and stationary with permanent factors of disability.

VOCATIONAL REHABILITATION:
A. There is a need for vocational rehabilitation.  yes/no
B. There is no need for vocational rehabilitation.  yes/no
C. The need for vocational rehabilitation cannot be determined at
   this time.

RETURN VISIT: __ D for Days __ W for Weeks __ M for Month  PRN
Reason for return visit:  X-ray  COX  Recheck  Suture removal
Staple removal  Test results  Surgery  Video Review  Post Op  H & P

→ 332

DISCUSSION: The treatment program was reviewed. Physical therapy has been continued to include: strengthening, range of motion, and knee program 3 times a week for 3 weeks. Present medication prescribed: Vicodin. I have given the patient a prescription for a thermophore for her lumbar spine pain, due to physical therapy for the right knee.

CURRENT STATUS: The patient is not working.

DISABILITY STATUS: The patient is temporarily totally disabled.

RETURN VISIT: The patient will return in 1 week for a post-op visit.

Sincerely,

*Fig. 20*

DATE

NAME
ADDRESS
STATE  ZIP

→ 330

Re:
Emp:
DOI:
SS#:
Cl#:

Dear Sir/Madam:

HISTORY: The patient is a xx-year-old Caucasian female who is returning for a postoperative visit, regarding complaints referable to the knee. The patient was injured in a work related accident on xx/xx/xx. The patient was last seen on xx/xx/xx. The patient underwent an arthroscopy, partial lateral and medial meniscectomy, and chondral debridement of the right knee on xx/xx/xx.

CURRENT COMPLAINTS: The right knee pain is a dull aching type. Other symptoms include: stiffness, soreness, numbness, and swelling. Her pain is improved by ice. Her pain is made worse by standing, walking, and bending.
The patient has night pain which renders her unable to sleep.

SPECIAL STUDIES: None.
ALLERGIES: No known drug allergies.
CURRENT MEDICATION: Motrin.

PHYSICAL EXAMINATION:
KNEE EXAMINATION:          Right
Flexion/Extension:         0-120   degrees X-RAY: None taken today.

DIAGNOSIS:
836.0   Medial meniscus tear, post arthroscopy, partial medial meniscectomy with chondral debridement, right knee.
836.1   Lateral meniscus tear, post arthroscopy, partial lateral meniscectomy, right knee.
716.96  Osteoarthritis of the right knee.

*Fig. 19*

DATE
NAME
ADDRESS
STATE Z/D

XX/XX/XX
RE:

HISTORY: The patient is a xx-year-old Caucasian male who is returning for a follow-up visit, regarding complaints referable to the hips. The patient was last seen on xx/xx/xx. Since his last visit he has taken a Medrol Dose Pack.

CURRENT COMPLAINTS: The patient denies any right hip pain. This has improved since his last visit.

The patient's left hip pain is a dull aching type. Other symptoms include soreness. This has improved since his last visit. His pain is improved by rest and medication. His pain is made worse by sitting, lifting, twisting, bending, and walking. The patient does not have night pain which awakens him.

SPECIAL STUDIES: None.

ALLERGIES: Codeine and Penicillin.

CURRENT MEDICATION: Antibiotics, Lanoxin, and Tagamet.

PHYSICAL EXAMINATION:
HIPS:          Right           Left
Flexion:       0-90 degrees    0-90 degrees
Areas of tenderness:    none   ischial tuberosity, left
Areas of erythema:      none   none
Areas of swelling:      none   none
Areas of ecchymosis:    none   none X-RAY: None taken today.

DIAGNOSIS:
912.00 Abrasion of the left arm, healed.

716.95 Osteoarthritis, post total hip arthroplasty, left.

820.21 Greater trochanter fracture, right hip.

DISCUSSION: The treatment program was reviewed. No physical therapy was ordered.

CURRENT STATUS: The patient is retired.

RETURN VISIT: The patient will return in 2 weeks for a follow-up visit.

Figures 24, 25:
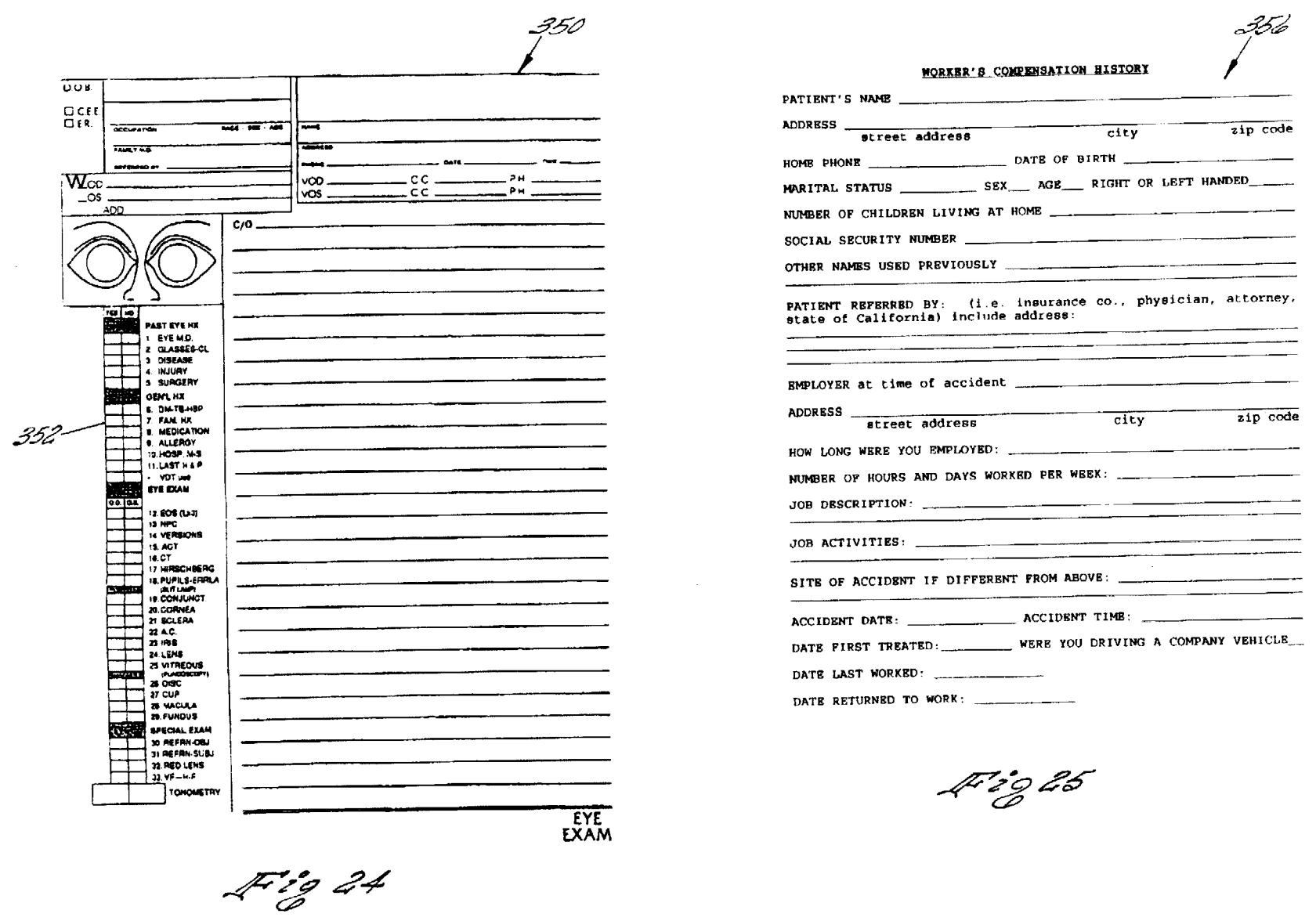

WORKER'S COMPENSATION HISTORY

PATIENT'S NAME _____

ADDRESS _____street address_____ _____city_____ _____zip code_____

HOME PHONE _____ DATE OF BIRTH _____

MARITAL STATUS _____ SEX _____ AGE _____ RIGHT OR LEFT HANDED _____

NUMBER OF CHILDREN LIVING AT HOME _____

SOCIAL SECURITY NUMBER _____

OTHER NAMES USED PREVIOUSLY _____

PATIENT REFERRED BY: (i.e. insurance co., physician, attorney, state of California) include address: _____

EMPLOYER at time of accident _____

ADDRESS _____street address_____ _____city_____ _____zip code_____

HOW LONG WERE YOU EMPLOYED: _____

NUMBER OF HOURS AND DAYS WORKED PER WEEK: _____

JOB DESCRIPTION: _____

JOB ACTIVITIES: _____

SITE OF ACCIDENT IF DIFFERENT FROM ABOVE: _____

ACCIDENT DATE: _____ ACCIDENT TIME: _____

DATE FIRST TREATED: _____ WERE YOU DRIVING A COMPANY VEHICLE _____

DATE LAST WORKED: _____

DATE RETURNED TO WORK: _____

EYE EXAM

↙ 358

ARE YOU PRESENTLY WORKING: YES ___ NO ___

WORK RESTRICTIONS, IF ANY: _____

PRESENT EMPLOYER: _____

ADDRESS: _____ street address _____ city _____ zip code

DATE OF EMPLOYMENT: _____

PHONE: _____

JOB DESCRIPTION _____

JOB ACTIVITIES _____

HISTORY OF THE ACCIDENT:

Describe fully the accident: _____

Describe any equipment and/or machinery involved: _____

Describe your physical complaints <u>immediately</u> following this accident: _____

Head: _____

Neck: _____

Back: _____

Arms: _____

Legs: _____

Worker's Compensation
Page 2

Did you report the injury to your employer? Yes ___ No ___

To whom and when did you report this injury? _____

Were you treated at the company dispensary, given first aid, or sent elsewhere? _____

Name and addresses of witnesses to the accident _____

How did you get to a place of treatment? _____

Did you go home or continue working? Yes ___ No ___

TYPE OF TREATMENT RECEIVED SINCE THE ACCIDENT: (include hospital, surgeries, physical therapy, chiropractic therapy or any other treatment)

| DOCTOR OR FACILITY | WHEN SEEN | NATURE OF TREATMENT | DID TREATMENT HELP? Y N | X-RAYS TAKEN Y N |
|---|---|---|---|---|
| | | | | |
| | | | | |
| | | | | |
| | | | | |
| | | | | |

Other tests performed: (MRI, CT scans, arthrogram, EMG)

Yes ___ No ___

List where tests were performed below: _____

Worker's Compensation
Page 3

*Fig 27*

What medications have been prescribed and give results:

MEDICATION        RESULTS
_____    _____
_____    _____
_____    _____

DIAGNOSIS GIVEN: _____
_____
_____

Describe fully all present complaints:

COMPLAINT    (IMPROVED/WORSE/UNCHANGED)    PAIN RATING
                                              (0-10)

Head: _____

Neck: _____

Back: _____

Arms: _____

Legs: _____

IF YOU HAVE HEADACHES PLEASE ANSWER THE FOLLOWING QUESTIONS:
How often do you have headaches? _____
How long do they last? _____
Do you have
(circle appropriate symptom(s)) Light-headedness, ringing in
ears, visual blurring, nervousness, or trouble sleeping.

Worker's Compensation
Page 4

What part of your head hurts? _____

What (if any) medications do you take for the headache and how
often do you take them? _____

IF YOU HAVE NECK PAIN PLEASE ANSWER THE FOLLOWING QUESTIONS:
(circle appropriate symptom(s)) bending head forward, looking up,
turning head from side to side, reaching up, lifting, pushing, or
pulling.

IF YOU HAVE BACK PAIN, PLEASE ANSWER THE FOLLOWING QUESTIONS:
How long can you sit in one place before the back pain becomes
intolerable? _____

How long can you stand in one place before the back pain is
intolerable? _____

How long can you walk before the back pain is intolerable? _____

How long can you remain bent over to do repeated bending before the
back pain is intolerable? _____

What is the greatest weight you can lift without increasing your
back pain? _____

Does overhead work, reaching, pushing or pulling cause an increase
in the back pain? _____

Worker's Compensation
Page 5

Fig 29

PRIOR WORK RELATED INJURIES:

List prior or past illnesses and/or surgeries. List name and addresses of employers (include dates and nature of injury, fractures, lacerations, contusions, auto accidents).

_____
_____
_____
_____

List dates you stopped working because of this accident. _____

Did you return to work? Yes___ No___

If so, date you returned to work? _____

Work restrictions if any? _____

Does the pain go into your arms or legs, if yes, which ones _____ and what activities cause this to occur? _____

Do you experience numbness in the legs, if yes (does it)

1. travel down the front of the legs? _____
2. travel down the back of the legs? _____
3. travel into the toes, if yes, which ones _____
4. is the numbness present constantly _____
5. when did this symptom start _____

ALL PATIENTS PLEASE ANSWER THE FOLLOWING QUESTIONS:

What medications are you currently taking? _____

Do you have other mental, physical, or emotional problems which might have caused, been aggravated, or resulted from this accident? _____

RESTRICTED SOCIAL ACTIVITIES:

List any social/sports activities that you can no longer do or have had to significantly limit due to this injury (i.e.: housework, gardening, child care)

ACTIVITY               DESCRIBE HOW YOU ARE RESTRICTED
_____
_____

*Fig 30*

PAST MEDICAL HISTORY -- Indicate if you have had any of the following:

```
                                    Yes      No
Measles, Mumps, Chickenpox    _____
Eye Problems                  _____
Ear, Nose, Throat Problems    _____
Respiratory Problems          _____
Cancer                        _____
Heart Disease                 _____
High Blood Pressure           _____
Arthritis                     _____
Gout                          _____
Urinary/Kidney Problems       _____
Liver Disease                 _____
Stroke                        _____
Diabetes                      _____
Epilepsy                      _____
Circulation Problems          _____
Stomach/Ulcer Problems        _____
Alcoholism/Drug Abuse         _____
Psychological Problems        _____
```

Industrial Injuries -- Have you ever been injured on the job other than what you are being examined for today?

Yes ____   No ____

If yes, please list below:

```
                                           DID YOU    IF NOT,
YEAR   EMPLOYER   INJURED AREA             RECOVER?   DESCRIBE
_____
_____
_____
```

PRIOR PERSONAL INJURIES:

Automobile Accidents -- Please indicate if you have ever been involved in one either before or after the date of accident for which you are being seen.

Yes ____   No ____

If yes, please list below:

```
                                           DID YOU    IF NOT,
YEAR   INJURED AREA/BODY PART              RECOVER?   DESCRIBE
_____
_____
```

Other Injuries -- List any major accidents/injuries other than listed above (includes broken bones).

```
                                           DID YOU    IF NOT
YEAR   INJURED AREA/BODY PART              RECOVER?   DESCRIBE
_____
_____
_____
```

Surgeries -- List any surgeries you have had performed.

```
YEAR   AREA OF BODY    DID YOU RECOVER?   IF NOT, LIST REASON
_____
_____
```

List any allergies to foods or medications _____

If you smoke cigarettes how long have you smoked and how much do you smoke? _____

Fig 33

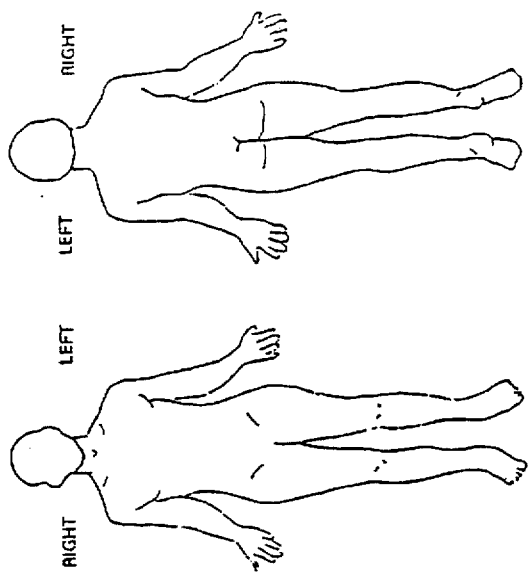

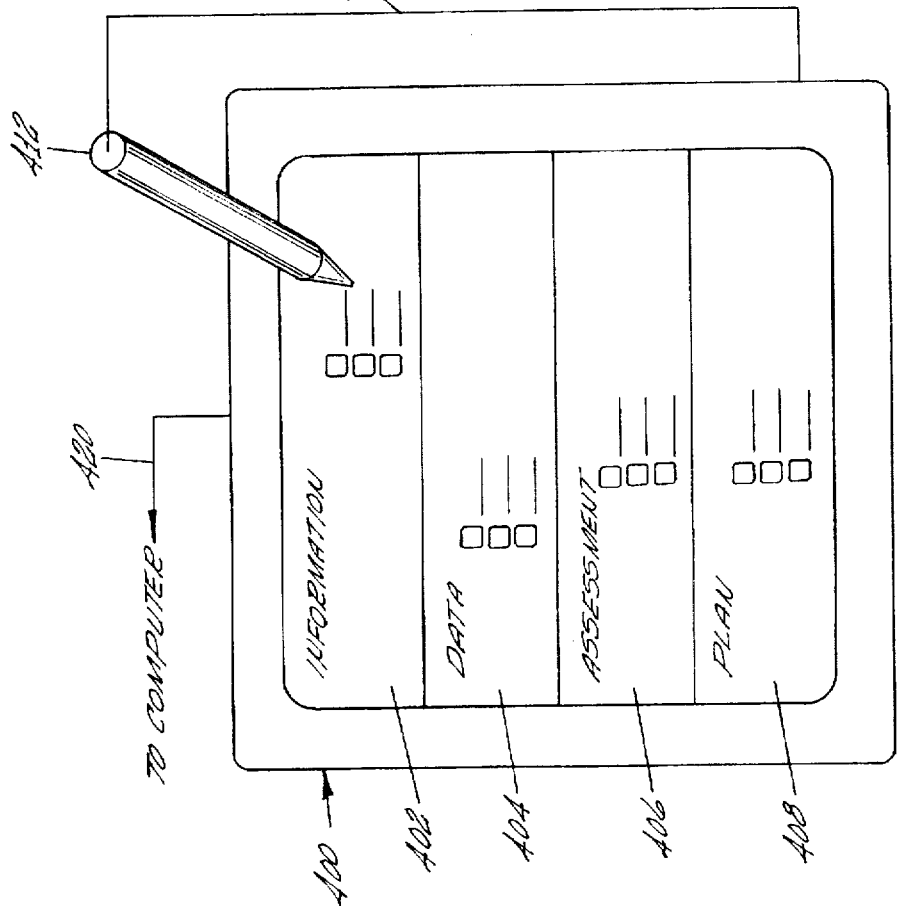

MEDICAL HISTORY DOCUMENTATION SYSTEM AND METHOD

A portion of the disclosure of this patent document contains material which is subject to copyright protection. The copyright owner has no objection to the reproduction by anyone of the patent disclosure, as it appears in the Patent and Trademark Office Patent files or records, but otherwise reserves all copyright rights whatsoever.

BACKGROUND OF THE INVENTION

1. Field of the Invention

This invention relates to a documentation system and method, and more particularly to a medical history documentation system having a recording apparatus which is used, in the preferred embodiment, by a writer to record in encoded indicia verbal information communicated by a healthcare person to the writer during a physical examination of a patient. The verbal information conveys at least one of the patient's current medical condition, the patient's physical condition, the patient's diagnosis and the patient's treatment plan. The medical history documentation system can be either a manual system, a computerized system or a combination of a manual system and computerized system. The method includes a step of comparing the recorded data with the encoded indicia recorded by the writer on the recording apparatus to insure accuracy and validity of the relevant information. The method also includes a step of verification wherein the results of the comparing step are verified upon completion to insure that proper comparison decisions have been made. This provides a validation step for quality assurance, legal and medical purposes.

2. Description of the Prior Art

Historically, healthcare professionals, such as doctors, nurses and other medical personnel, personally record medical information for a patient using personal handwritten notes or on forms. Such patient information is developed during discussions with and the physical examination of a patient. The forms and/or patient reports generated from the forms and notes are typically stored in patient's history file.

In medical offices and clinics, a patient is typically required to complete a questionnaire which discloses personal information about a patient, including background medical information and pre-existing medical conditions. The questionnaire may also establish a patient's current medical condition. A patient's history file is opened and contains the completed questionnaire along with other documents.

As part of the physical examination, the healthcare person makes a determination as to the medical condition of a patient and this is generally referred to as the Patient Diagnosis. Also, the healthcare person makes a determination as to how a diagnosed medical condition is to be treated medically and this is generally referred to as a Patient Treatment Plan.

When a patient is physically examined by a healthcare professional, the results of the physical examination are typically recorded personally by the physician or healthcare professional entering the information manually onto a form which is then placed in the patient's history file. Also, it is common practice for the healthcare person to make hand notes during the patient's physical examination. The hand notes are later used by the healthcare person for personally dictating a patient's report. The dictation is then transcribed, reviewed and signed by the healthcare person who conducted the patient's physical examination.

The practice of dictating and transcribing is widely used to record information in the medical field. Healthcare professionals have been increasingly burdened by the need to document every encounter with patients. Physicians must record information about each patient's office visit, diagnosis, suggested treatment and prescription given. In addition to recording patient's information, physicians must fill out forms for submission to insurance companies and provide information to regulatory agencies. Physicians spend a significant portion of their work day gathering and dictating the needed information for each record or form. Further, a physician must maintain a staff to transcribe the information into reports and fill out required forms.

There are severest medical history documentation systems known in the art which are intended to more efficiently and effectively gather and/or document medical information for a patient.

U.S. Pat. No. 4,428,733 discloses an information gathering system used for obtaining medical information from a patient. The system has one or more question sheets bearing a set of questions, usually medical questions written in the language of the patient. A separate answer sheet is provided, upon which the patient provides answers to the questions. The answer sheet has information concerning each possible answer. The information on the answer sheet may be in a different language than the language of the question sheet. A mechanism is preferably provided for positioning and holding the answer sheet in a predetermined position relative to the question sheets to enable the patient to see the information on the answer sheet as well as the questions.

U.S. Pat. No. 4,221,404 discloses a medical history record filing system which includes a plurality of attachment sheets for holding medical test records and a plurality of medical record sheets.

Each medical record set includes a plurality of separable portions and at least one of the plurality of separable portions is adapted to be attached to one of the attachment sheets. The record sets and the attachment sheets are color coded to indicate the type of medical test that is to be performed and recorded. The separable portion of the medical records is adapted to be attached to a medical record attachment sheet and has provisions for locating the separable portion in a chronological order on the medical record attachment sheet. Each medical record set has provisions for the physician to personally indicate or record the type of tests desired that are to be conducted, the urgency of the request and other pertinent information. In addition, each medical record set has provisions for the laboratory or a person who is analyzing the test results to record test data. Provisions related to the test desired are separated vertically from the provisions related to the test results. The separable portions of the medical record sets are so designed that when a series of them are attached to the attachment sheet only the test results and related information are normally visible on the medical record attachment sheet. One or more medical record attachment sheets and the associated portions of the medical record set can be located in one file folder.

U.S. Pat. No. 3,913,118 discloses a process and apparatus for accurately recording medical and personal information obtained from a medical patient or a prescription customer. The purpose of the process and apparatus is for expediting accounting and bookkeeping procedures related to the medical treatment or prescription services furnished the patient or customer. A transparent matrix has pre-printed thereon in permanent ink portion of a form for recording information to be submitted for payment to a medical program for professional services rendered to the patient or member of the program. The matrix also includes a means forming a pocket thereon for receiving and holding an identification card or other information bearing form, such as a prescription order or the like. The pocket holds the form in position relative to the pre-printed material on the matrix such that the identification information appears through the transparent matrix at a prescribed location relative to the remainder of the form. The so assembled matrix having the form in the pocket is then copied on a copying machine producing a reproduction of the matrix and form as a document containing patient's specific information for use in accounting and bookkeeping purposes.

U.S. Pat. No. 4,991,091 discloses a self-contained apparatus used personally by a physician during patient examination. The apparatus is battery operated and can be reprogrammed to alter or modify examination information or produce a permanent record of examination results. The apparatus includes a penboard which includes microprocessor based controller with internal memory having prestored thereon sets of specific examination indicia which are displayed by liquid crystal displays ("LCDs"). The patient's name is displayed on an LCD. Associated with the specific examination indicia are one or more light emitting diodes ("LEDs") and corresponding bar codes which represent permanently pre-printed indicia representations.

General information diagnosis categories are identified by suitable words such as "Vital Signs". Also, LEDs and bar codes are provided for general examination and treatment categories such as, for example, "Chemistry Profile". The bar codes are used with a light pen for optically identifying the corresponding category and the LED adjacent to each category indicia are illuminated for indicating the category selected by the physician.

The controller includes suitable memory for storing patient examination information, for controlled programming of the operating panel and for down loading data to a central computer. Input to the microcontroller is also provided by a light pen that is manipulated by the physician for scanning one or more bar code panels.

The concept is based on the examining physician personally using the penboard, light pen and microprocessor during the examination procedure to record medical information.

U.S. Pat. No. 5,267,155 describes a document generation system which automates the documentation process in the medical field. The system provides a computer based documentation system incorporating a retrievable database with a menu driver and graphic window environment. The documentation system utilizes previously defined document templates or "boiler-plates" to manage Patient Reports and includes user interface for use in selecting phrases to be inserted in the template.

The system contemplates that the physician personally conducts a patient examination and either generates personal notes which the physician can use later for dictation or the physician personally fills out a checklist.

In this manner, the physician reports of the patient examination can vary for each patient. The input for the report is prepared directly by the physician and can contain any number of variable responses. Each variable response may include different options, such as options on a menu of a computer. The physician can then personally modify and customize the report document throughout by inserting words into the generated document with the use of an integrated word processor.

When the physician personally completes a checklist, another individual can generate the desired document from information checked off by the physician on the checklist.

SUMMARY OF THE INVENTION

The medical documentation system and method described herein is a new, novel and unique invention. In the preferred embodiment, the invention is used as a medical history documentation system. The method of using the system represents a significant change in concept and enables a patient's medical documentation to be accurately and efficiently prepared.

In the preferred embodiment, the medical documentation system includes a medical history documentation system comprising a recording member having a plurality of discrete recording sections formed thereon. Each of the discrete recording sections are programmed to record information relating to at least one of a designated patient's current medical condition, a physical examination, a diagnosis and a treatment plan. An input member is used by a second person for recording medical information which is communicated, e.g., verbally, by sign language or other communication technique, by a first person to the second person during a physical examination of the designated patient by the first person. The information being entered on the recording member is in the form of predetermined encoded indicia in at least one discrete recording section of the recording member. The system includes a transcriber for providing a plurality of report section templates. The plurality of report sections include: (i) a first report section template corresponding to a discrete recording section for the patient's current medical condition; (ii) a second report section template corresponding to a discrete recording section for the patient's physical examination; (iii) a third report section template corresponding to a discrete recording section for the patient's diagnosis; and (iv) a fourth report section template corresponding to a discrete recording section for the patient's treatment plan. Each of the report section templates comprise a plurality of optional text variable segments each of which are assigned to a selected one of the predetermined encoded indicia. The transcriber is operative to decode each one of the predetermined encoded indicia recorded on the recording member into the optional text variable segment assigned thereto for each applicable discrete recording section. An imaging device, responsive to the transcriber, prepares a patient's report specific to the designated patient. The patient report comprises a combination of selected optional text variable segments for a designated patient's at least one of medical condition, physical examination, diagnosis and treatment plan. In a computerized system the transcriber may include a computer which includes programming for the decoding of the encoded indicia into the optional text variable segments corresponding to each one of the predetermined encoded indicia.

A method for documenting verified patient's medical information for a patient's history file using the medical documentation system is also new, novel and unique. The method comprising the steps of: (i) conducting by a first person a physical examination of a patient in accordance with an examination procedure wherein the first person during the physical examination of the patient communicates the patient's medical information to be documented; (ii) recording by a second person with a recording device in a predetermined format the patient's medical information communicated by the first person during the physical examination of the patient; (iii) processing the patient's medical information recorded by the recording device to produce in a programmable format a patient report containing the patient's medical information; and (iv) comparing the patient's medical information on the patient report with the patient's medical information recorded by the recording device to verify the accuracy of the patient's medical information on the patient report.

There are several important and significant problems with the known prior art documentation systems and methods. As discussed above, one of the most important limitations of each of the above systems and methods for documenting patient information is that the physician typically dictates a report on each patient encounter. The dictated report, subsequently, must be typed by a transcriber. The process is time consuming and repetitive, causing reports to be incomplete. As a result, potential legal and insurance problems as well as reduced quality of patient care can occur.

When a physician or other healthcare person uses traditional manual methods of record keeping, patient data is not readily available for fast an easy review. A patient's medical record cannot be easily combined with other reports or other patient data for analysis and reporting.

Third party medical providers and insurance companies as well as governmental entities are undergoing significant changes in order to contain and/or reduce the cost of medical treatment while constantly improving the delivery and quality of medical services.

As a result of these changes the present apparatus, systems and methods for documenting medical information tend to set a limit on the number of patients that a healthcare professional can service. This limit is directly related to the time and effort required by the healthcare professional for documenting a patient's current medical condition, the results of a physical examination, a diagnosis and a treatment plan.

Typically, a doctor spends a substantial portion of time each day, sometimes up to 50% of time during the day, in reviewing patient's notes, dictating patient reports and reviewing the final transcribed patient reports before the same are filed in the patient's history file. Typically, a doctor examines in the order of 20 to 25 patients per day using the currently available systems.

As pressure is placed on organizations such as hospitals, health maintenance organizations ("HMOs"), clinics and medical facilities to process and service a higher number or volume of patients per day, the quality of both delivered services and patient documentation tends to be sacrificed.

If the healthcare professional uses personal notes and/or forms, such as a checklist, then the person conducting the examination personally takes time to dictate the patient's report. The dictation must be typed. The healthcare professional must personally take time to review, edit and finalize the report. For quality control purposes, the healthcare professional is also responsible for personally taking time to verify the accuracy of the dictation and transcription by comparing the patient reports to the personal notes and/or a checklist form.

Therefore, it is clear that one problem that has developed is the amount of time a healthcare professional needs to personally devote to preparing documentation. The time required has become significant, and takes away from time that could otherwise be expended providing patient services. If the healthcare professional is required or demanded by an HMO, clinic or medical facility to treat a larger volume of patients, compliance with such demands includes an attended increase in the patient documentation requirements. As a result, it is apparent that the healthcare professional cannot continue using the presently known medical documentation systems and methods in order to meet such demands. The healthcare professional is placed in the position where, on one hand, more patients must be processed per day while, on the other hand, the healthcare professional is obligated to promptly provide accurate and complete patient documentation to meet legal, insurance and third party medical service providers requirements.

The known processes of medical documentation systems and methods are based on the healthcare professional, for example a physician, surgeon, nurse or other healthcare professional performing both the examination of the patients and, concurrently during the examination, making personal notes, personally filling out forms or using a more sophisticated approaches such as the documentation systems described in U.S. Pat. Nos. 4,991,091 and 5,267,155. Documentation systems disclosed and taught by U.S. Pat. Nos. 4,428,733, 4,221,404 and 3,913,118 are used primarily for accounting and record keeping purposes and are not suited for recording the patient information relating to current medical conditions, physical examination results, a diagnosis or treatment plan.

In response to the above mentioned problem and needs, the present invention was developed.

The Medical Documentation System and Method of the present invention can be used in HMOs, clinics or medical facilities for the purpose of efficiently recording medical data of a patient during a diagnostic examination by a healthcare professional and promptly producing a final patient report documenting current medical conditions, the results of a physical examination, a diagnosis, treatment plan and/or charges.

The medical documentation system and method of the present invention unshackles the healthcare professional from the burden of the current patient medical documentation system limitations while enabling the healthcare professional to examine up to double the number of patients compared to the present systems. Concurrently, by a high quality medical history documentation system and accurate patient medical reports and files are maintained.

One advantage of the present invention is that the medical documentation system and method can be used in an HMO, clinic and medical facility environment wherein each healthcare professional assigned the responsibility of treating in the order of about 40 or more patients a day can do so while maintaining the integrity of the patient's history file.

Another advantage of the present invention is that the medical history documentation system can be used with a second person functioning as a writer or recorder and chaperone who is present during the physical examination and/or patient treatment performed by a first person who is the healthcare professional. The writer records on a recording device, in precoded indicia, patient information. During the patient's examination or treatment session, the healthcare professional verbally communicates, sometimes in key words, to the writer the results of the patient's examination, a diagnosis and treatment plan. All of this is accomplished without the healthcare professional having to make personal notes, filling out forms or otherwise taking time to write down information.

Another advantage of the present invention is that the medical history documentation system can be a manual system, that is, the writer can use a preprinted form to record the encoded indicia representing the patient's information. The writer can decode the encoded indicia and dictate and/or transcribe the patient report.

Another advantage of the present invention is that the medical documentation system can be a manual system which is used as an input into a computer. The writer can use a preprinted form to record the encoded indicia representing the patient's information. The preprinted form can then be scanned into a computer system which translates or decodes the encoded indicia. The encoded indicia is assigned an optional text variable segment. When the computer decodes the encoded indicia, the assigned optional text variable segments are stored in memory in a retrievable format.

Another advantage of the present invention is that the medical history documentation system can be a combination manual system and computer system. The writer can use a preprinted form to record the encoded indicia representing the patient's information. The preprinted form can then be scanned into a processor which includes a computer system which translates the encoded indicia. The computer can be programmed to have a plurality of report section templates including a first report section template corresponding to a recording section for the patient's current medical condition, a second report section template corresponding to a recording section for the patient's physical examination, a third report section template corresponding to a recording section for the patient's diagnosis and a fourth report section template corresponding to a recording section for the patient's treatment plan. Each of the report section templates comprises optional text variable segments each of which are assigned to a selected one of the predetermined encoded indicia. The processor is operative to decode each one of the predetermined encoded indicia into its assigned optional text variable segment in each applicable discrete recording section and storing the same in a retrievable format.

Another advantage of the present invention is that the medical history documentation system can be a completely computerized system. The writer can use a computer input device, such as a preprogrammed input device having the forms stored therein which are analogous to preprinted form, and an electronic input device to mark or program the input device with encoded indicia to record the patient's information. The encoded indicia entered into input device is then down loaded into a processor which includes a computer system which translates the encoded indicia. The computer can be programmed to have a plurality of report section templates including a first report section template corresponding to a recording section for the patient's current medical condition, a second report section template corresponding to a recording section for the patient's physical examination, a third report section template corresponding to a recording section for the patient's diagnosis and a fourth report section template corresponding to a recording section for the patient's treatment plan. Each of the report section templates comprises optional text variable segments each of which are assigned to a selected one of the predetermined encoded indicia. The processor is operative to decode each one of the predetermined encoded indicia into its assigned optional text variable segment in each applicable discrete recording section and storing the same in a retrievable format.

Another advantage of the present invention is that the medical documentation system includes, as a part thereof, a combination of an apparatus for recording information using encoded indicia representing the patient's information and input device which is operative with the apparatus. The input device is used by a second person functioning as a writer or recorder who is present during the physical examination and/or patient treatment performed by a first person who is the healthcare professional. The writer utilizes the input device to record patient information in the apparatus in predetermined encoded indicia. During the patient's examination or treatment session, the healthcare professional verbally communicates, sometimes in key words, to the writer the results of the patient's examination, a diagnosis and treatment plan.

Another advantage of this invention is that the computer used in the system may include a comparator for comparing the optional text variable segment to the encoded indicia recorded on the computer input device. In addition, the computer can be programmed to verify the results of the comparison for accuracy and validity. All of these steps provide a quality assurance control to insure accuracy and validity of the patient report.

Another advantage of the present invention is that a method for documenting information, preferably medical information, using the documentation system results in a new, novel and unique method which can be used as documentation.

Another advantage of the present invention is that a method for documenting verified patient medical information for a patient's history file is provided. The method includes the steps of conducting by a first person a physical examination of a patient; recording by a second person with a recording device in a predetermined format the patient medical information communicated by the first person during the physical examination of the patient; processing the patient medical information recorded by the recording device to produce in a programmable format a patient report containing the patient medical information; and comparing the patient medical information on the patient report with the patient's medical information recorded by the recording device to verify the accuracy of the patient's medical information on the patient report.

Another advantage of the present invention is that the method for documenting verified patient medical information for a patient's history fill is provided. The method can further include the step of determining if the results of the comparison show that the accuracy of the patient's medical information is verified or unverified. The step of comparing further comprises the step of determining if the comparison step shows that the accuracy of the patient medical information is unverified, and if so, correcting the patient medical information to make the same verified.

BRIEF DESCRIPTION OF THE DRAWINGS

These and other advantages of the invention will be readily apparent when considered in light of the detailed description hereinafter of the preferred embodiment and of the drawings which include the following figures:

FIG. 7 is a pictorial representation of a preprinted form used by a second person or writer for recording in predetermined encoded indicia a patient's current medical information and the results of a physical examination conducted by a first person, usually a healthcare professional, and communicated verbally to the second person;

FIG. 8 is a pictorial representation of a preprinted form used by a second person or writer for recording in predetermined encoded indicia additional information of a patient's current medical information determined during a physical examination, a diagnosis and a treatment plan communicated verbally to the second person by the first person;

FIG. 9 is a pictorial representation of a preprinted form used by a second person or writer for recording in predetermined encoded indicia additional information of a patient's current medical information and an assessment of a patient made during the physical examination communicated verbally to the second person by the first person;

FIG. 10 is a pictorial representation of a preprinted form for recording patient's history for a new patient or established patient with a new history, the results of which are used as an input by a second person or writer for recording in predetermined encoded indicia additional information of a patient's current medical information;

FIGS. 11 through 18 are pictorial representation of a series of preprinted forms which include at least one discrete reporting section for recording information relating to an orthopedic and gynecological examination of a designated patient and which is used by a second person or writer for recording in predetermined encoded indicia patient information of a patient's current medical information and an assessment communicated verbally to the second person by the first person during the physical examination;

FIGS. 19 and 20 are pictorial representations of a two page final patient report generated by a processor which decoded each of the predetermined encoded indicia into its assigned optional text variable segments in each applicable discrete recording section and which has been printed out in a final report by an imaging device;

FIG. 21 is a pictorial representation of another embodiment of a single page final patient report generated by a processor which decoded each of the predetermined encoded indicia into its assigned optional text variable segments in each applicable discrete recording section and which has been printed out in a final report by an imaging device;

FIGS. 22 and 23 are pictorial representations of a series of preprinted forms which include at least one discrete reporting section for recording the information relating to a gynecology examination of the designated patient and which is used by a second person or writer for recording in predetermined encoded indicia patient information of a patient's current medical information and an assessment communicated verbally to the second person by the first person during the physical examination;

FIG. 24 is a pictorial representation of a preprinted form which includes at least one discrete reporting section for recording information relating to an ophthalmologic examination of a designated patient and which is used by a second person or writer for recording in predetermined encoded indicia patient information of a patient's current medical information and an assessment communicated verbally to the second person by the first person during the physical examination;

FIGS. 25 through 36 are pictorial representations of a series of preprinted forms which include at least one discrete reporting section for recording the information relating to a general examination including an urological examination for a workmen's compensation of a designated patient and which is used by a second person or writer for recording in predetermined encoded indicia patient information of a patient's current medical information and an assessment communicated verbally to the second person by the first person during the physical examination to produce a worker's compensation history; and FIG. 37 is a pictorial representation of a recording member in the form of a computer input device having a plurality of discrete recording sections formed thereon, each of said discrete recording sections being programmed to record information relating to at least one of a designated patient's current medical condition, a physical examination, a diagnosis and treatment plan and an input member used by the second person for recording medical information verbally communicated by the first person to the second person during a physical examination of the designated patient.

DESCRIPTION OF THE PREFERRED EMBODIMENT

Figure 1:
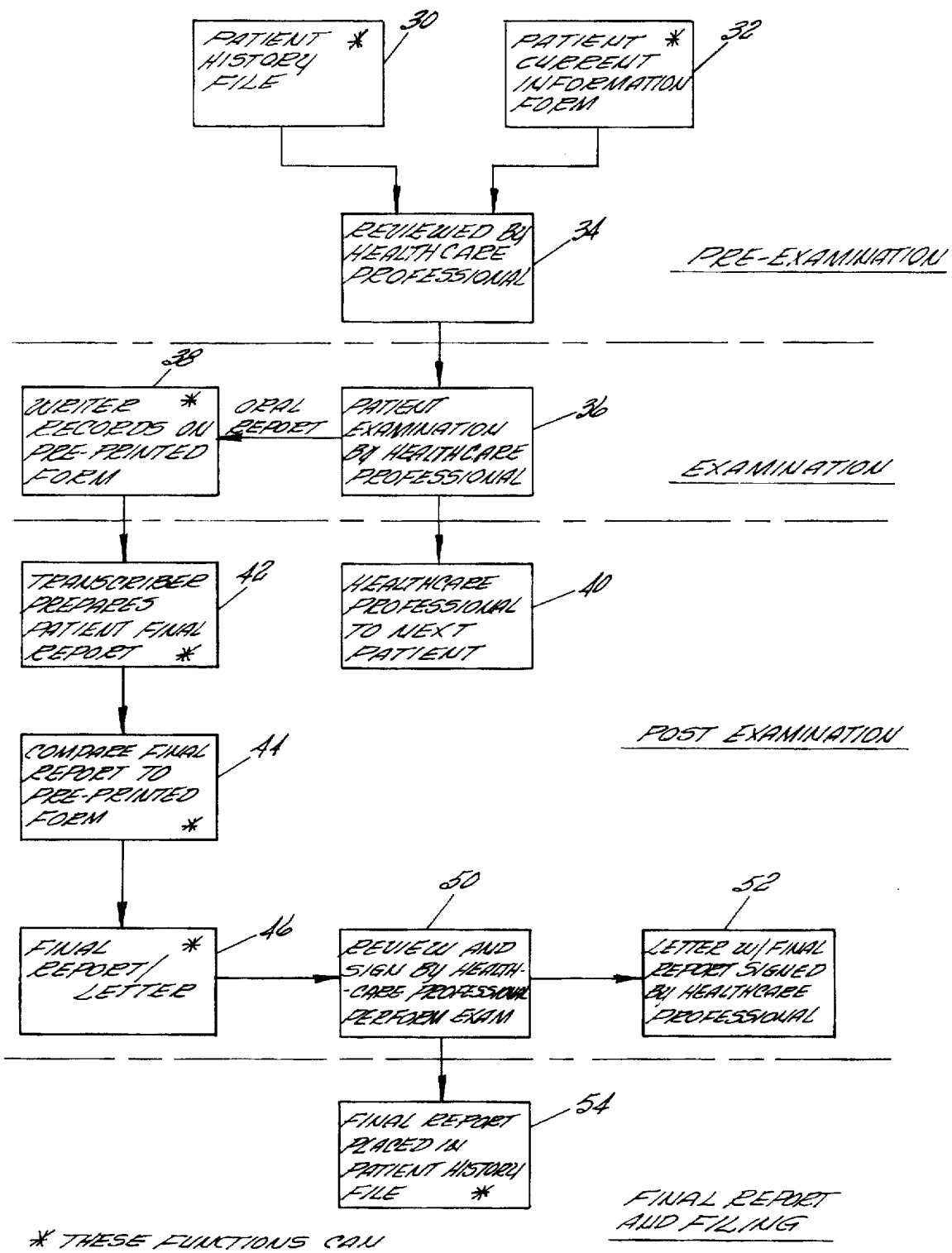
FIG. 1 is a schematic diagram of the stages of the medical documentation system of the present invention as used in a typical medical facility comprising a pre-examination stage, an examination stage, a post examination stage and final report and filing stage.

Before commencing with a description of the medical history documentation system, a description of the basic concepts of the medical history documentation system will first be presented. The method described below has several inherent opportunities during each step for insuring accuracy and validity of the recorded patient data.

TYPICAL USE OF MEDICAL HISTORY DOCUMENTATION SYSTEM AND METHOD

In an overview, the medical documentation system and method used in a medical facility such as an HMO, clinic or other medical clinical environment is based on the following concept and procedures:

1. A Current Patient History form is completed prior to the examination by the patient or by a staff person talking with the patient. This includes identifying the reason for the visit and other patient medical problems and/or complaints. This helps to identify the important medical data to be recorded during the patient examination. The original patient file is then combined with the current Patient History File and the healthcare professional reviews the same prior to beginning the examination.

2. Thereafter, the patient is given a physical examination by an appropriate healthcare professional. During the examination, there are typically three (3) persons present who are: (i) the designated patient; (ii) the healthcare professional conducting the physical examination who is typically the highly compensated individual; and (iii) a writer who is a trained staff writer or recorder who is typically at a lower level of compensation. The healthcare professional, sometimes referred to herein as the first person, conducts the physical examination of a patient in accordance with an examination procedure. The first person during the performance of the physical examination of the patient communicates, preferably verbally, by the writer, sometimes referred to herein as the second person, the patient medical information to be documented by the writer.

3. During the examination, if the healthcare professional forgets or inadvertently omits a part of the pre-established examination or fails to obtain the required medical data, the writer can immediately bring this to the attention of the healthcare professional and the omitted data is immediately obtained to avoid the necessity for a re-examination.

4. The writer uses a preprinted form which is specially designed to capture the data in a prescribed encoded indicia format. This reduces the possibility of error. A computer terminal may be used instead of a preprinted form.

5. A transcriber or processor uses the preprinted form or input from the computer, if a computer terminal is used for processing the patient's medical information, to produce in a programmable format a patient report containing the patient's medical information.

6. The processor or transcriber compares the patient's medical information on the patient report with the patient's medical information recorded by the recording device in the predetermined encoded indicia to verify the accuracy of the patient's medical information on the patient report.

7. In a manual system, the writer may dictate a patient's Final Report Form using the data from the preprinted form which is then translated into predetermined optional text variable segments to generate the final patient report.

8. In a computer system or a combination manual and computer system, the computer system could "read" the preprinted form or process the data entered via a computer terminal. The input data is compared, either by an operator or by a verification program, to insure accuracy of the data.

9. The method for documenting verified patient medical information during a medical examination to produce a final report for filing in a patient history file is generally accomplished as follows:

(a) The healthcare professional conducts a physical examination of a patient in accordance with an examination procedure and the healthcare professional verbalizes, during the physical examination, the patient's medical information to be documented using prearranged key words, statement and remarks;

(b) A writer, who accompanies the healthcare professional, records in a predetermined format with a recording device (e.g., a preprinted form or computer terminal) the patient's medical information verbalized by the healthcare professional during the physical examination of a patient;

(c) The patient's medical information recorded by the recording device is used by a computer operator or a computer program to produce a patient Final Report Form containing the patient's medical information in a programmable format;

(d) A comparison is made of the patient's medical information on the patient Report Form with the patient information recorded by the recording device to verify the integrity of the patient's medical information on the patient report form compared to the patient medical information recorded in the recording device; and (e) The healthcare professional who conducted the physical examination reviews and signs the verified patient's Final Report Form before it is entered into a patient's history file.

10. The healthcare person reviews and signs the Patient Report Form either immediately after examining the patient or a few hours after examining the patient. If an error is present on the medical report, the healthcare professional would have a high probability of detecting the error because the patient examination is very fresh in the mind of the healthcare professional.

11. When an existing patient history file is matched up with the current Patient History Form, a staff member reviews the file for accuracy and to verify that all of the documents and records in that patient's history file are correct and complete.

12. The Medical Documentation System can be programmed to automatically output patient reports in a form for filing in the patient file or in a letter form when necessary, e.g., Worker's Compensation reports, letters to Attorneys or other parties.

TRAINING AND ASSISTANCE

Members of a healthcare professional staff can be trained to properly complete the preprinted forms, to function as a writer, to transcribe as a computer operator, to function as a staff interviewer and be trained for other related functions. With training and experience, the efficiency of each person performing a specific function is increased and the accuracy and validity of the system is likewise increased. With the appropriate quality assurance review, an efficient, accurate and verified Medical Documentation System and Method exists which meets the ever-increasing demands of the medical profession.

ANCILLARY BENEFITS

Other ancillary benefits may result, such as for example, the addition of healthcare reimbursement codes to the system. The Medical Documentation System and Method can help automatic billing procedures due to its preprogrammed format features while reducing errors.

MEDICAL HISTORY DOCUMENTATION SYSTEM FOR A TYPICAL MEDICAL FACILITY

FIG. 1 shows in a schematic diagram the stages of the medical documentation system of the present invention. In FIG. 1, a pre-examination stage utilizes a Patient History File 30. The Patient History File 30 may be a new file established for a new patient and may include a patient questionnaire. If the patient is other than a new patient, the Patient History File 30 would include all prior documentation. Also, documentation in the form of a Patient Current Information Form 32, which may be a New Patient History form or, if the patient is an established patient; an Established Patient With a New Injury form is obtained or completed by the staff and patient. The Patient History Form 30 and the Patient Current Information Form 32 are combined and reviewed by the healthcare professional as part of the pre-examination stage shown generally by Box 34.

The following stage is referred to as the Examination Stage and is so identified in FIG. 1.

In the Examination Stage, the participants are the patient, writer and healthcare professional who is to conduct the examination, diagnosis and treatment plan. The step of the Patient Examination By Healthcare Professional is designated by 36.

The healthcare professional conducts a physical examination of a patient in accordance with an examination procedure. During the physical examination, the healthcare professional communicates to the writer, preferably by an oral report and verbalization, the patient's medical information to be documented using prearranged key words, statements and remarks.

The writer, who accompanies the healthcare professional, records in a predetermined format with a recording device, for example the writer Records On a Preprinted Form 38 (or on a computer input apparatus), the patient's medical information verbalized by the health-care professional during the physical examination of a patient.

The use of a writer has an additional advantage. If the healthcare professional forgets or inadvertently omits a part of the pre-established examination or fails to obtain the required medical data during the examination, the writer can immediately bring this to the attention of the healthcare professional and the omitted data is immediately obtained to avoid the necessity for a re-examination.

This completes the examination phase.

The next phase is identified as the Post Examination Stage and is so identified in FIG. 1. As is shown by the Box 40 labeled Healthcare Professional to Next Patient, the healthcare professional then conducts a physical examination of the next patient. A significant and important part of this medical history documentation system is that the healthcare professionals do not spend any portion of their time making notes, filling out forms or the like. Since the healthcare professional is typically highly compensated relative to the writer, the healthcare professional's time is utilized more efficiently in examining patients, performing diagnosis and prescribing a patient treatment plan.

Typically, a physician in a medical office or clinic can service approximately 20 to 25 patients. The reason is that the physician is required to personally record patient information, record patient data, make notes or complete preprinted forms. By eliminating this task from the physicians, or other healthcare professionals, the number of patients that can be serviced can be increased substantially and in some instances can be doubled. In some medical facilities, healthcare professionals can service in the order of 40 to 45 patients per day which is nearly a 100% increase.

The reason that this increase in efficiency of the healthcare professional can be obtained is illustrated by the next sequence of events illustrated in FIG. 1. In the Post Examination Stage, the writer then utilizes the information from a preprinted form as an input to a transcriber. In a manual system, the writer may dictate the encoded indicia recorded on the preprinted form using certain pre-established words and phrases. The transcriber prepares a patient final report as depicted by Box 42. The transcriber may utilize a known word processing system and have templates of optional variable text segments which the transcriber would select or program, essentially decoding the key words and phrases to produce a final report.

When the transcriber has prepared the patient final report, the transcriber or writer then compares the final report to the encoded indicia recorded on the preprinted form, which is depicted by Box 44, to ensure that the final report is accurate.

The final report is then prepared by an imaging device and may be in the form of a patient report to be filed in a patient's history file or in the form of a letter to be sent to a third party as depicted by Box 46.

The final report or letter, as depicted by Box 46, is then reviewed and signed by the healthcare professional who performed the examination of the patient. If the medical history documentation system is a manual system using a transcriber as described above, the healthcare professional would review all patient reports at the end of the day.

If the medical history documentation system is a computerized system, e.g., a scanner is used to scan the preprinted form and scan the predetermined encoded indicia as an input to the computer, the healthcare professional can be provided a final report or letter for review and sign upon completion of the physical examination of the patient as depicted by Box 50.

Upon completion of the review by the healthcare professional, the letter with the final report, as depicted by Box 52, is signed and mailed to the party requiring the same. The final patient report is placed in the patient's history file and this is depicted by Box 54 in the final report and filing stage.

In FIG. 1, the steps or functions represented by the Boxes 30, 32, 38, 42, 44, 46 and 54 can be performed with a computer input device, a computer and/or software.

Figure 2:
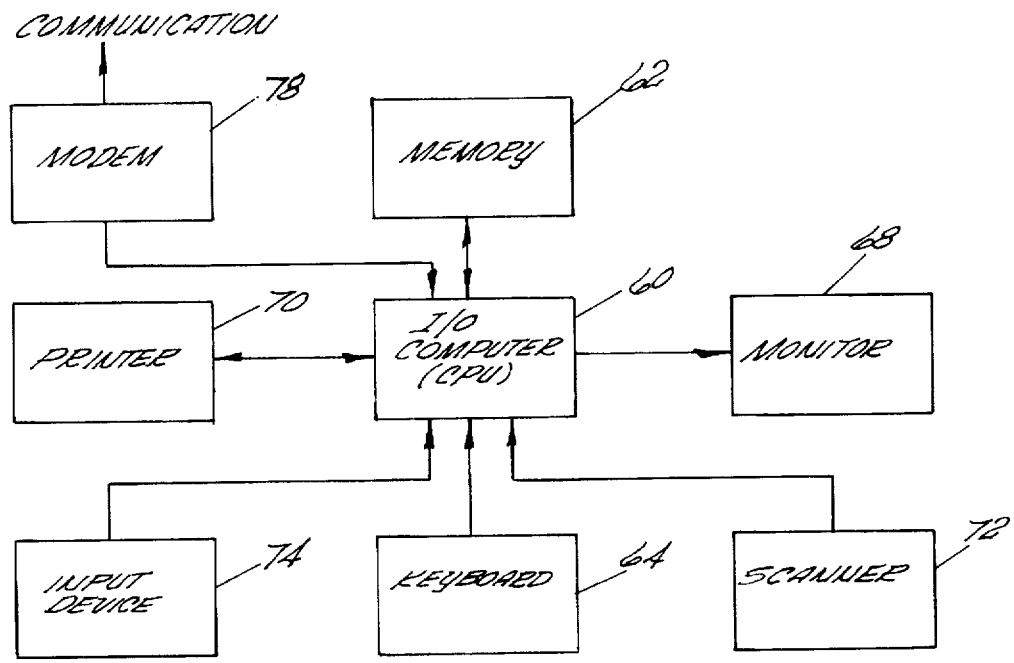
FIG. 2 is a block diagram of a computerized documentation system practicing the teachings of the documentation system of the present invention.

FIG. 2 illustrates a block diagram of a processor which is a computerized documentation system for practicing the invention including the method disclosed herein. In the preferred embodiment, the documentation system is utilized for a medical history documentation system. However, the basic documentation system and method has other applications and can be used in other professions having similar documentation requirements.

The processor includes a central processing unit (CPU) 60 which has an input/output controller for communicating with a wide variety of input and output devices. The CPU 60 is operatively connected to a memory 62 which can be in the form of a random access memory, a hard disk drive, a floppy disk drive, a compact disk drive or the like. A keyboard 64 is used for programming and controlling the CPU 60 and the input/output devices.

A monitor 68 is operatively connected to the CPU 60 and can be used as a display device for producing on the monitor an image representing patient information. Also, a printer 70 is operatively connected to the CPU 60 and can be used to produce printed patient reports or letters to third parties as required for documenting the patient information.

Other input devices such as a scanner 72 and any other specialized input device 74, such as for example the specialized apparatus illustrated in FIG. 37, may be operatively connected to the CPU 60. Also, a modem 78 may be operatively connected to the CPU to transmit and receive data electronically.

All of the above components are well known in the art and are available for use in a documentation system using the teachings of the present invention. Of course, appropriate programming and software would be required to program and control the CPU 60, memory 62, keyboard 64, monitor 68, printer 70 and input/output devices 72, 74 and 78.

Figure 3:
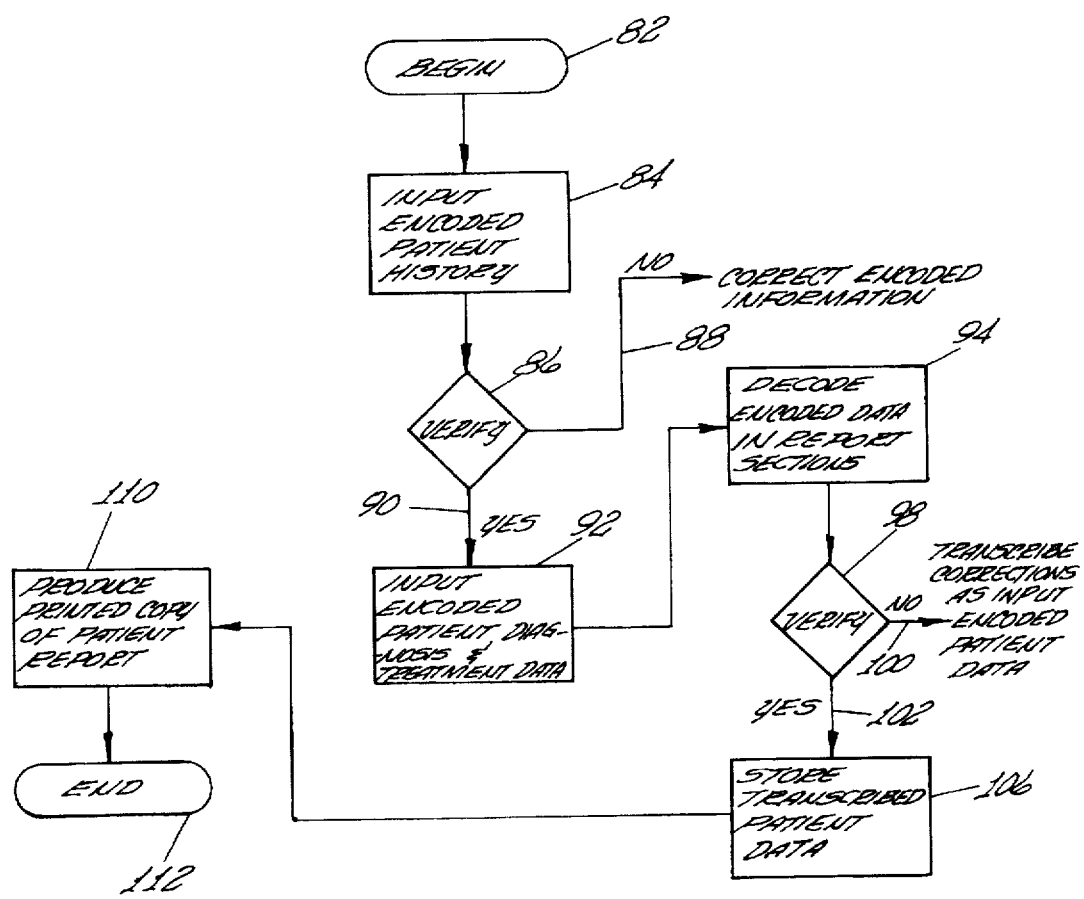
FIG. 3 is a software flow chart showing the programming of a computer system illustrated in FIG. 2 for a medical documentation system.

The software flow chart of FIG. 3 shows the basic programming chart or diagram for a computer system illustrated in FIG. 2 for a medical documentation system. In FIG. 2, the step of Begin 82 covers the function of the writer in preparing the patient's history using predetermined encoded indicia. The encoded indicia is then entered as an input into the computer system as illustrated by step 84. The encoded indicia is then compared to the input to verify that the encoded indicia is accurate which is shown by step 86. If the input is not verified, then the error is noted which is depicted by line 88 and the encoded indicia or information is corrected to match the encoded indicia comprising the input to the computer.

If step 86 verifies that the encoding step is accurate, then the encoded data is combined as shown by line 90 with the encoded indicia representing the patient diagnosis and treatment data shown generally as Box 92. The input encoded data is decoded by the computer into optional variable text segments assigned to each encoded indicia by report sections as is depicted by step 94. The results of the decoding of data in each report section is again verified as is shown by step 98. If the decoding is not verified, it is corrected as shown by line 100. If the decoding is verified, it is then stored shown by line 102 as transcribed patient data in a retrievable format as depicted by step 106. The stored data can then be generated a printed copy in the form of a patient report as depicted by step 110. Upon generation of the final report and storing the same in memory, the process is completed as depicted by end 112.

Figure 4:
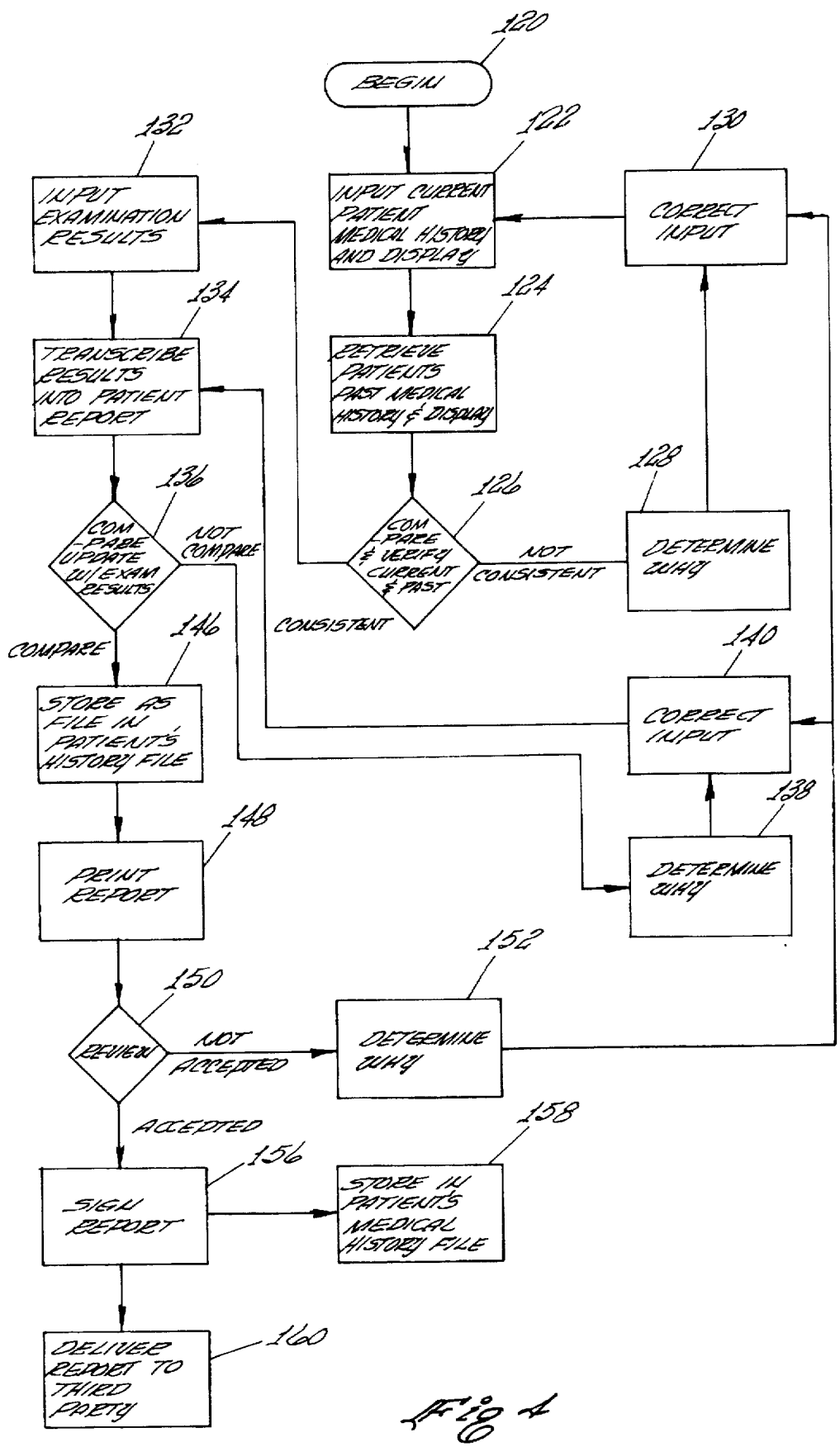
FIG. 4 is a software flow chart showing the programming of a computer system illustrated in FIG. 2 for a medical history documentation system including quality control programming steps.

FIG. 4 is a software flow chart showing the programming of a computer system illustrated in FIG. 2 for a medical history documentation system including a quality control programming.

In the software flow chart of FIG. 4, the Begin step is shown as 120. The current patient's medical history is entered as input data and displayed on the computer system as depicted by step 122. The display can be viewed and verified to the information set forth on the patient's information form. The patient's history file comprising past medical records and history can be retrieved and displayed as depicted by step 124. The data can be verified electronically or visually as depicted by step 126. If the information is not verified, the reason why is determined as shown by step 128 and the information is corrected as shown by step 130 and the corrected input having the data is re-entered as an input to the current history causing a repeat of step 122. This cycle is repeated until the data is correct.

Upon the input data being verified, the data is combined with the input from the examination results as depicted by step 132. The data is decoded and transcribed into data representing optional variable text segments representing the data from each discrete report section on the input form or device as depicted by step 134. The decoded data and information is again compared to the encoded indicia to verify that the decoding is accurate as depicted by step 136. If the verification determines that the decoding and comparison is not correct, that is a "not compare" determination is made, then a determination is made as to why the same is not correct, as depicted by step 138, and the data and information is corrected as depicted by step 140. Depending on the error, the corrected data is then returned as an input to step 136 or as an input to step 122.

After the comparison determines that the data and information is accurate, or a "compare" condition exists, the data and information is stored in a retrievable memory as a file in the patient's history file depicted by step 146. A patient report, depicted by step 148, is prepared. The patient report is reviewed by the healthcare professional as depicted by review 150. If the report is not accepted, a "not approved" decision is and a determination is made as to why the final report was not accepted as shown by step 152. Depending upon the error, the corrected data is then returned as an input to step 134 or as an input to step 122.

If the final report is approved, an "accepted" decision is made and the report is delivered to a third party and stored in the patient's history file as depicted by steps 158 and 160.

Figure 5:
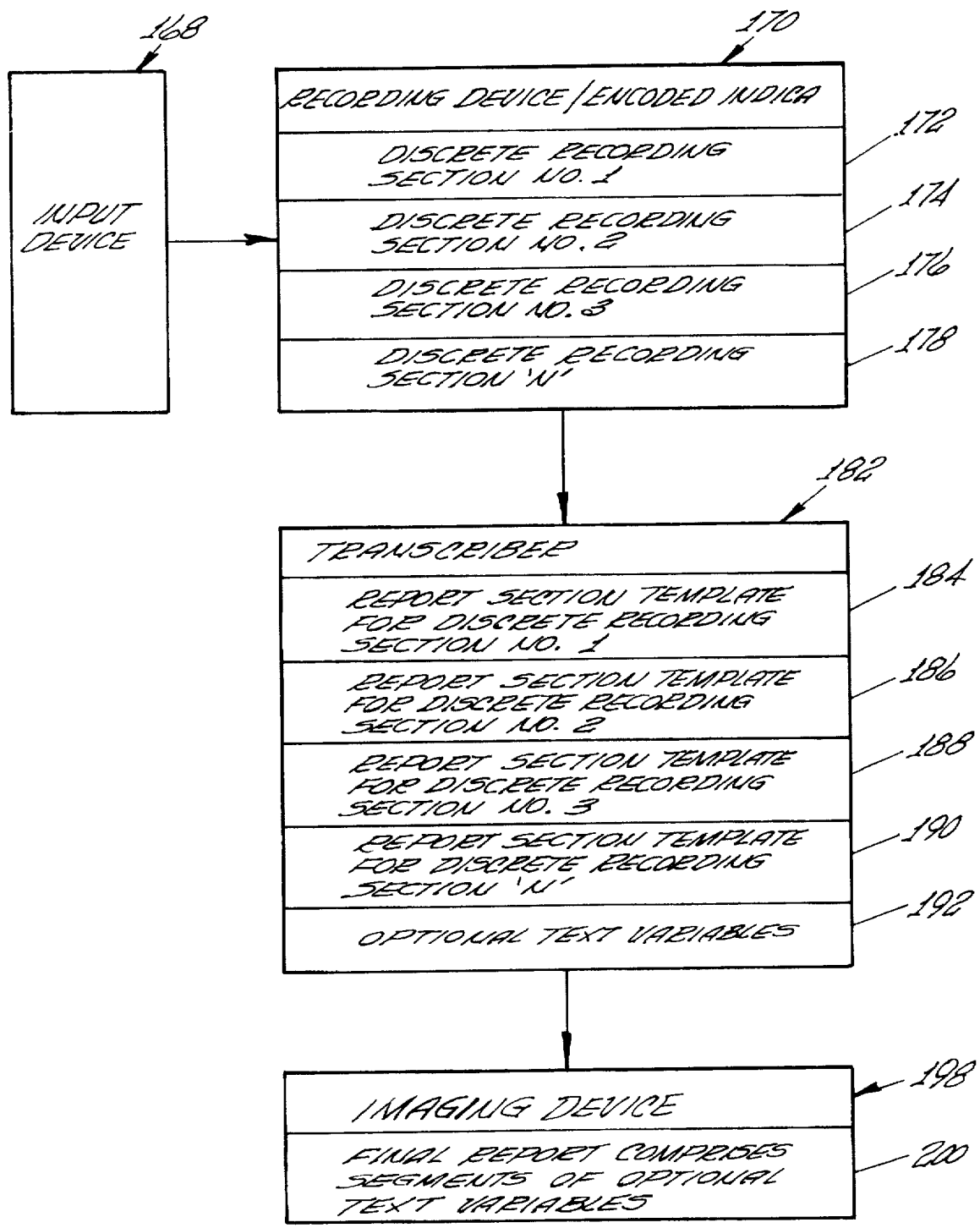
FIG. 5 is a pictorial diagram of a basic computer apparatus having an input device, a recording device, a transcriber and an imaging device for performing the medical history documentation of patient's information.

FIG. 5 is a pictorial diagram of a basic computer apparatus having an input device, a recording device, a transcriber and an imaging device for performing the medical history documentation of patient information.

In FIG. 5, the medical history documentation system includes an input device shown generally as 168 which is operative with a recording device or recording member shown generally as 170. The recording member 170 has a plurality of discrete recording sections 172, 174, 176 and 178 formed thereon recording section 178 is characterized as "N" Section. Each of the discrete recording sections 172, 174, 176 and 178 are programmed to record information relating to at least one of a designated patient's current medical condition, a physical examination, a diagnosis and a treatment plan.

The input member 170 is used by the second person for recording medical information communicated verbally by hand signs or other forms of communicating by the first person to the second person during a physical examination of the designated patient. The information is entered on the recording member 170 using the input device 168 in the form of predetermined encoded indicia in at least one discrete recording section of the recording member 170. Usually, but not necessarily, encoded indicia is entered into all four discrete sections 172, 174, 176 and 178.

A transcriber shown generally as 182 is used for providing a plurality of report section templates including a first report section template 184 corresponding to a discrete recording section for the patient's current medical condition, a second report section template 186 corresponding to a discrete recording section for the patient's physical examination, a third report section template 188 corresponding to a discrete recording section for the patient's diagnosis and an "N" Section, such as for example, a fourth report section template 190 corresponding to a discrete recording section for the patient's treatment plan. Each of said report section templates 184, 186, 188 and 190 comprise a plurality of optional text variable segments depicted by 192, each of which are assigned to a selected one of the predetermined encoded indicia. An example of a predetermined encoded indicia would be the alphanumeric "male-02". The optional variable text segment assigned to this alphanumeric could be as follows:

CURRENT COMPLAINTS: The patient denies any right hip pain. This has improved since his last visit.

The transcriber 182 is operative to decode each one of the predetermined encoded indicia recorded on the recording member 170 into the optional text variable segment assigned thereto for each applicable discrete recording section.

An imaging device shown generally as 198 is responsive to the transcriber 182 for preparing a patient's report shown generally as 200 specific to the designated patient. The patient report 200 comprises a combination of selected optional text variable segments for a designated patient's at least one of medical condition, physical examination, diagnosis and treatment plan.

Figure 6:
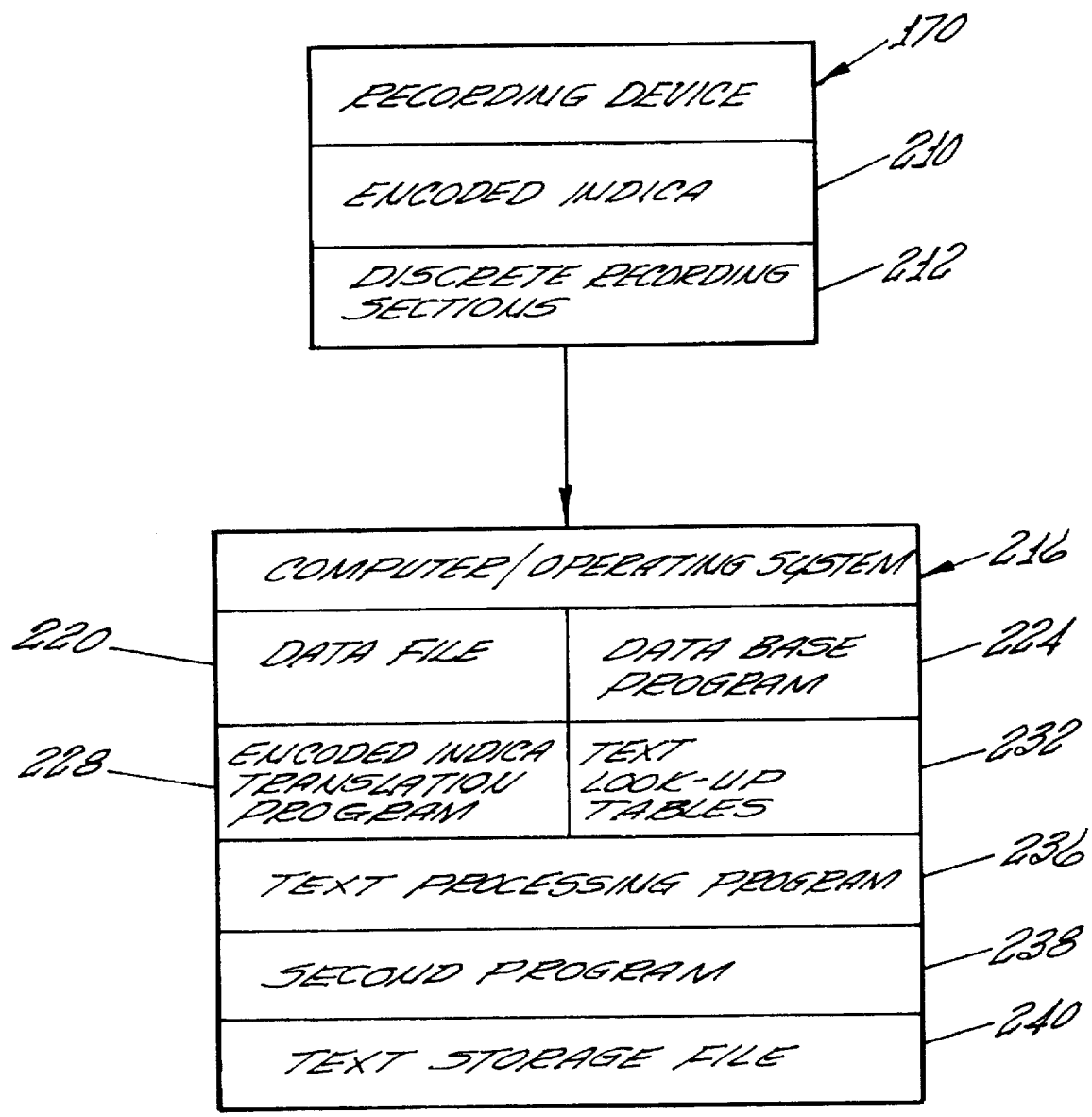
FIG. 6 is a pictorial diagram illustrating the information flow from the recording device into a processor comprising a computer/operating system which includes various data files, various computer programs, text look-up tables and storage for optional text segments representing the information of the documentation of a patient's medical history.

FIG. 6 is a pictorial diagram illustrating the information flow from the recording device 170 into a processor or computer/operating system shown generally as 216. The recording device 170 contains encoded indicia shown generally as 210 located in discrete recording sections 212. The processor or computer/operating system 216 includes one or more of the following: various data files 220, a data base program 224, encoded indicia translation programs 228, text look-up tables 232, text processing programs 236, e.g., Word for Windows 6.0, additional programs 238, e.g., billing or medical reimbursement code data, and text storage files 240. As such, the computer/operating system 216 includes programming for the decoding of the optional text variable segments corresponding to each one of the predetermined encoded indicia. The text look-up tables 236 can be used as a comparator for comparing the optional text variable segments to the encoded indicia recorded on the recording member 170. The second program can be used to enable the computer to verify the results of the comparison of the optional text variable segments with the encoded indicia recorded on the recording member 170.

Figures 7, 8:
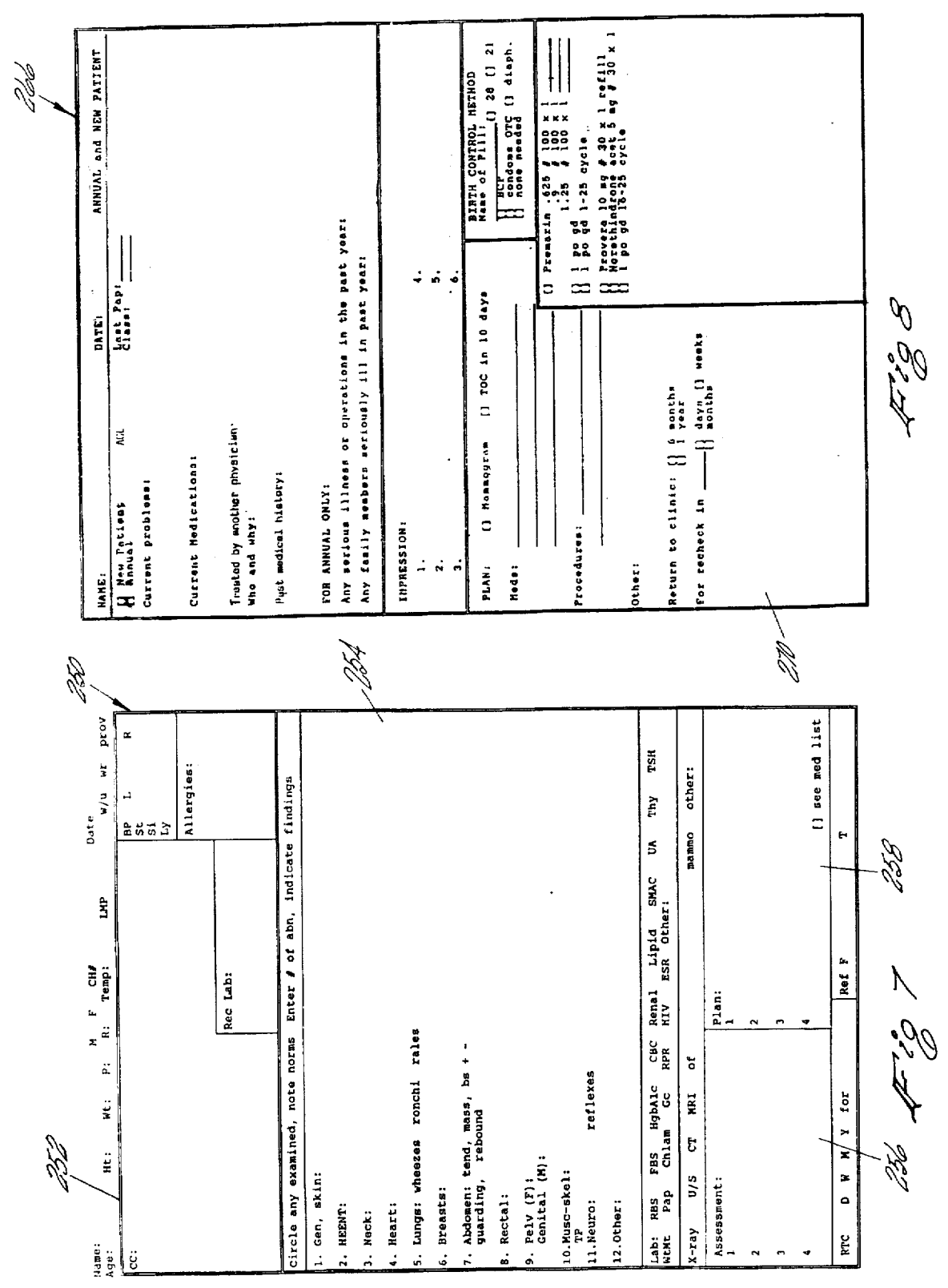

In FIG. 7, the pictorial representation illustrates one example of a preprinted form 250 used by a second person or writer for recording in predetermined encoded indicia a patient's current medical information, discrete section 252, and the results of a physical examination conducted by a first person, usually a healthcare professional, and communicated verbally to the second person, are recorded in discrete section 254. Discrete section 256 is used for a patient's assessment and discrete section 258 is used for a patient's treatment plan. The writer would record appropriate predetermined encoded indicia in each discrete section based on the results of a physical examination conducted by a first person, usually a healthcare professional, and communicated verbally to the second person.

In FIG. 8, the pictorial representation illustrates another embodiment of a preprinted form 266 used by a second person or writer for recording in predetermined encoded indicia additional information of a patient's current medical information determined during a physical examination, a diagnosis and a treatment plan communicated verbally to the second person by the first person. In the example of preprinted form 266, the patient treatment plan in discrete section 270 is specific for a female.

Figures 9, 10:
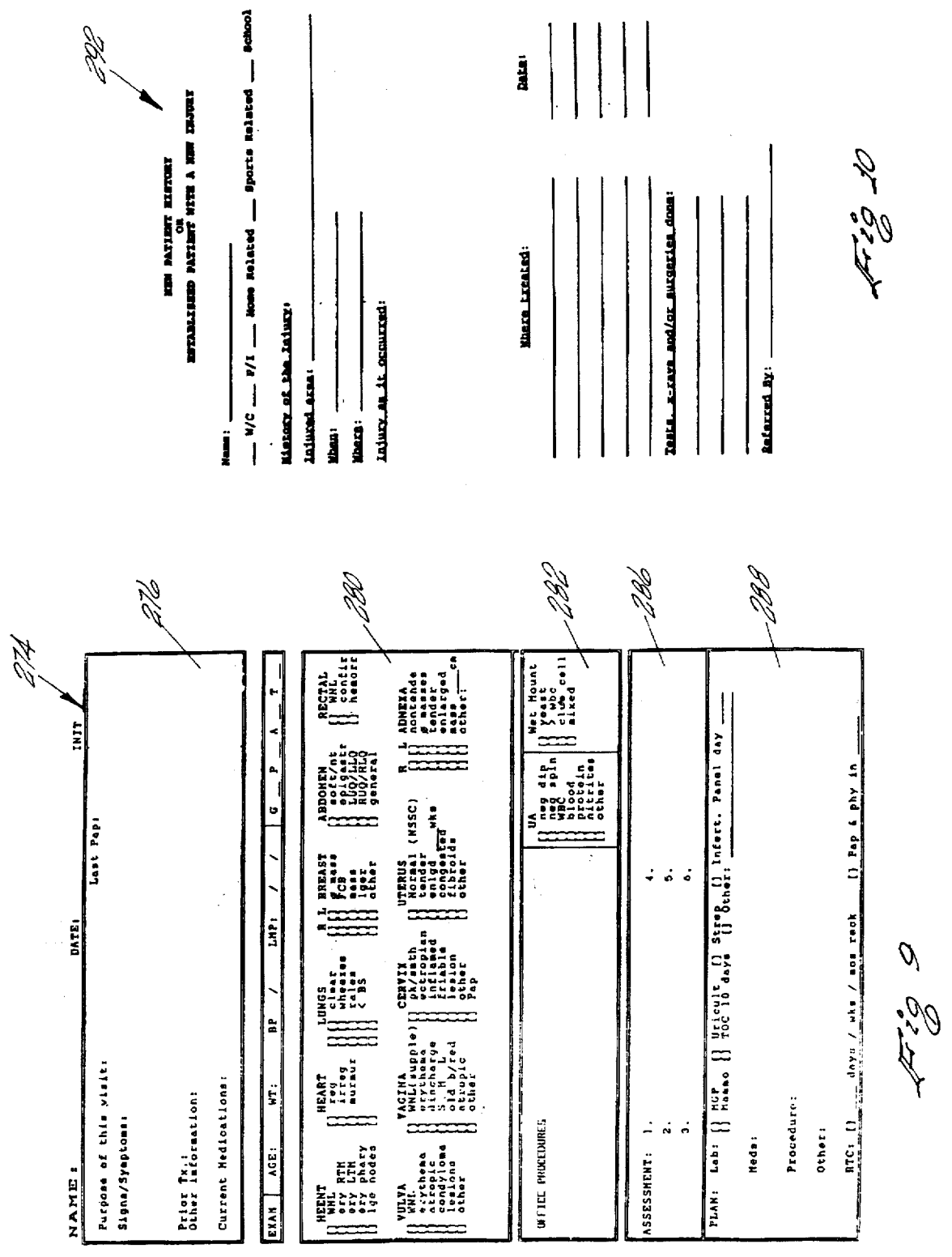

FIG. 9 illustrates as a pictorial representation another embodiment of a preprinted form 274 used by the second person or writer for recording in predetermined encoded indicia a patient's current medical information, discrete section 276, and the results of a physical examination conducted by the first person, usually a healthcare professional, and communicated verbally to the second person, in discrete section 280 and required office procedures in discrete section 282. Discrete section 286 is used for a patient's assessment and discrete section 288 is used for a patient's treatment plan. The writer would record appropriate predetermined encoded indicia in each discrete section based upon the results of a physical examination conducted by a first person, usually a healthcare professional, and communicated verbally to the second person.

FIG. 10 is a pictorial representation of a preprinted form 292 which is used for the dual purpose of recording a patient's history for a new patient or for an established patient with a new injury. The results of the encoded indicia on form 292 are used as an input for a patient's current medical information.

FIGS. 11 through 18 are pictorial representations of a series of detailed preprinted forms 300 through 314 comprising eight (8) pages for an orthopedic examination. Forms 300 through 314 lend themselves to a computerized system because of the detailed level of information required. Apparatus for recording data and an input device adapted as an input device to a computer system would enable the writer or second person to enter the information into the computer system using an input device during the examination.

FIGS. 19 and 20 are pictorial representations of a two page final patient report in letter form having two (2) pages identified as forms 330 and 332. These forms are generated by a processor which decoded each of the predetermined encoded indicia into its assigned optional text variable segments in each applicable discrete recording section and which has been printed out in a final report by an imaging device.

FIG. 21 is a pictorial representation of another embodiment of a single page final patient report 338 generated by a processor which decoded each of the predetermined encoded indicia into its assigned optional text variable segments in each applicable discrete recording section and which has been printed out in a final report by an imaging device. This form has the exemplary optional variable text segment for alphanumeric "male-02" which has been decoded or translated into Paragraph 2 which states:

CURRENT COMPLAINTS: The patient denies any right hip pain. This has improved since his last visit.

Figures 22, 23:
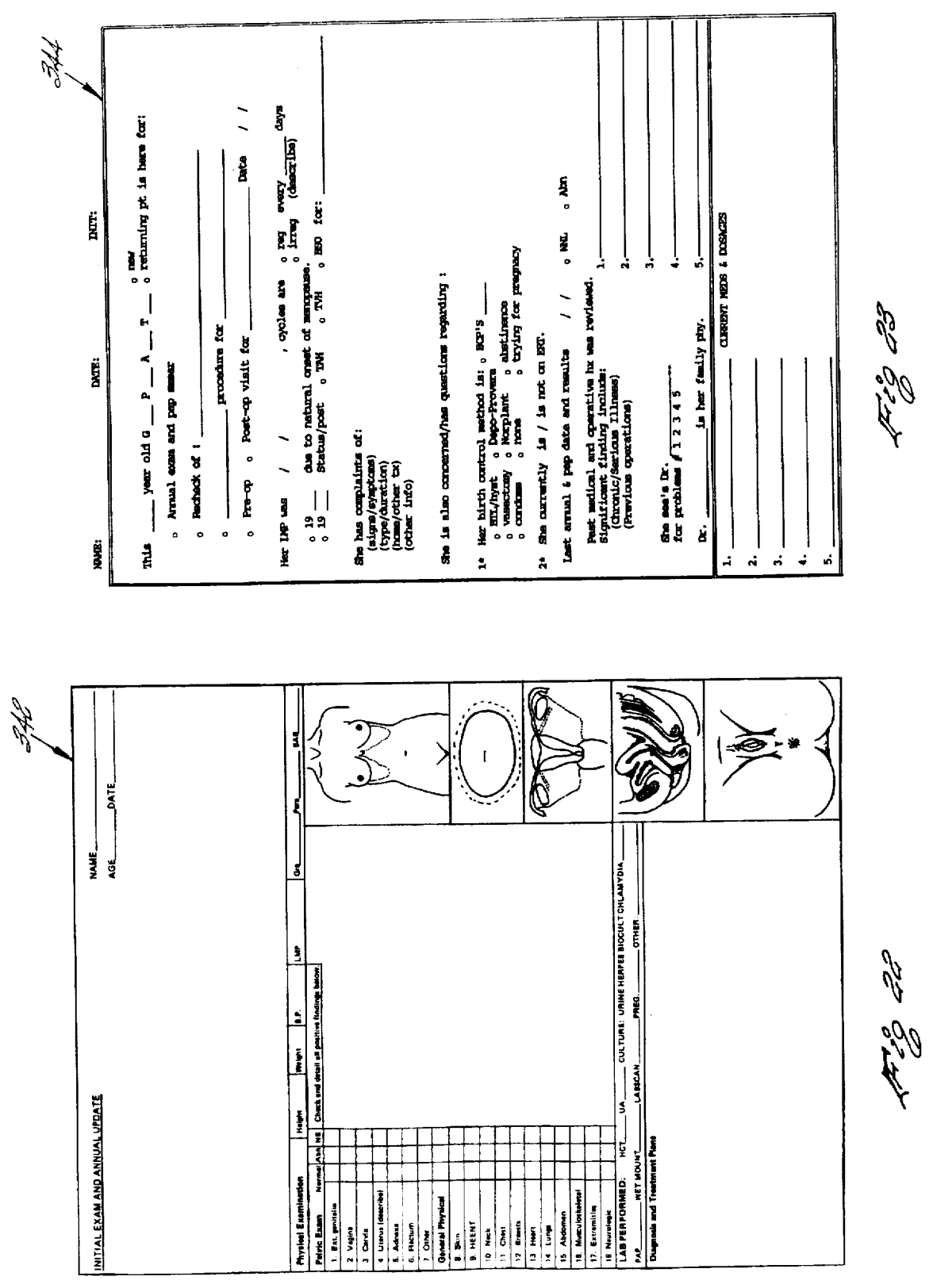

FIGS. 22 and 23 are pictorial representations of a series of two (2) preprinted forms 342 and 344 which include at least one discrete reporting section for recording the information relating to a gynecology examination of the designated patient and which is used by the second person or writer for recording in predetermined encoded indicia patient information of a patient's current medical information and an assessment communicated verbally to the second person by the first person during the physical examination.

FIG. 24 is a pictorial representation of a preprinted form 350 which includes at least one discrete reporting section 352 for recording information relating to an ophthalmologic examination of a designated patient and which is used by the second person or writer for recording in predetermined encoded indicia patient information of a patient's current medical information and an assessment communicated verbally to the second person by the first person during the physical examination.

FIGS. 25 through 36 are pictorial representations of a series of preprinted forms 356 through 378 which include at least one discrete reporting section for recording the information relating to a general examination for a workmen's compensation of a designated patient comprising eight (8) pages for an orthopedic examination. Forms 356 through 378 lend themselves to a computerized system because of the detailed level of information. Apparatus for recording data and an input device adapted as an input device to a computer system would enable the second person or writer to enter the information into the computer system using an input device during the examination. The forms 356 through 378 include discrete reporting sections for recording patient's history information relating to job related activities as well as information developed relating to pain and level of disability due to injuries. During examination of a designated patient, these forms are used by the second person or writer for recording in predetermined encoded indicia patient's information of a patient's current medical information and an assessment communicated verbally to the second person by the first person during the physical examination.

The above format could be adapted for other medical specialties and as, for example, urology, thoraoscopy, dermatology and the like. Such specialties would require a specific format for the recording member or recording device.

FIG. 37 is a pictorial representation of an input device to a computer in the form of a recording member or recording device 400 having a plurality of discrete recording sections 402, 404, 406 and 408 formed thereon. The recording device 400 is used in cooperation with an electrically operatively connected input device such as a light pen 412. In FIG. 37, the light pen 412 is electrically connected to the recording device 400 by lead 416. The recording device 400 is, in turn, electrically connected to a computer through conductor 420. The recording device 400 can be a simple input device to a computer and each entry is communicated or down loaded to the computer for storage and processing.

In the alternative, the recording device could contain its own microprocessor, memory and related input/output devices and be used to collect data and down load the same to a computer upon completion of the physical examination.

Also, the image depicted in FIG. 37 could be a page displayed on a monitor that is responsive to a light pen 412. The writer would use the light pen 412 to select the appropriate encoded indicia from a menu on the screen of the monitor. The computer would respond to the light pen 412 to store the encoded indicia and then process the same as described herein.

The computer also can include a means for verifying the comparison of the optional text variable segments with the encoded indicia. In a medical documentation system, with the comparison and verification steps, the quality assurance aspects of the system are at a high level for professional and legal liability reasons.

The preferred embodiment for the documentation system is as medical history documentation system. However, it is envisioned that the basic concepts could be used in other fields such a law, engineering and other professions and businesses where client or customer interviews and or examinations are conducted or required as part of a service process. The system and methods can be adapted for specific uses, e.g., in an operating room theater where a writer can record information communicated by a surgeon during a surgical procedure. The present trend is to provide medical services at the lowest possible level and costs. Procedures once performed in hospitals are now performed in surgical or out-patient clinics or facilities. With the constant demand for these facilities to reduce costs, it is reasonable to expect that certain procedures will be transferred to an office setting as authorized or mandated office procedures. As a result, office management will be required to have each healthcare professional service more patients to reduce costs and to manage healthcare expenses. Under certain HMO plans, a medical facility is provided a fixed, annual captivation fee per patient and the facility is obligated to provide all normal patient services with a fixed cost structure. As a result, it is becoming imperative that the higher paid healthcare professionals spend substantially all of their time in providing patient services and no time in preparing patient histories, reports and the like.

It is envisioned that writers could be trained and certified as medical writers in a formal training program to be efficient and have sufficient medical knowledge to effectively function with healthcare professionals.

The medical history documentation system and method disclosed herein is a major breakthrough enabling medical facilities to provide high quality services, to provide such services to the highest number of patients per healthcare professional as possible while maintaining a verified and validated reporting and patient history system.

In addition, the medical history documentation system can be customized to make the same more personal. For example, if a physician has a desired format for letters and reports or certain phrases and paragraphs that are important to that physician, the templates having the optional variable text segments can be tailored to or assigned specific encoded indicia such that the patient history file and/or letters contain the desired format and text that has been customized to the physician's requirements.

With the improvements in computer programming and the introduction of user friendly computer systems, the entire medical examination procedure can be automated using second person or a recorder without requiring the healthcare professional to personally perform the entry of patient data and information into the computer system which is the limitation of most medical systems including voice activated systems.

What is claimed is:

1. A documentation system comprising
    a preprinted form having a plurality of recording sections wherein each one of said plurality of recording sections is assigned as a discrete recording section for a designated condition in a selected printed format for recording information relating to its associated designated condition;
    a recording means for recording on the preprinted format and in the appropriate discrete recording section one of a predetermined encoded indicia representing information developed for a designated condition;
    an input member responsive to said recording means for recording information specific to the designated condition communicated to said recording means, said information being recorded in the form of encoded indicia in at least one discrete recording section of said input member;
    a transcriber responsive to said encoded indicia for providing at least one report section template corresponding to the discrete recording section for its associated designated condition, said report section comprising optional text variable segments each of which are assigned to one of said predetermined encoded indicia, said transcriber being responsive to said encoded indicia recorded in said at least one discrete report section to decode the optional text variable segment assigned to one of the predetermined encoded indicia; and
    a report prepared by the transcriber which is specific to each designated condition comprising optional text variable segments documenting the designated condition.

2. A medical documentation system comprising
    apparatus for recording information relating to at least one of a designated patient's current medical condition, a physical examination, a diagnosis and a treatment plan;
    an input device operative with said apparatus for recording medical information communicated by a first person to a second person during a physical examination of the designated patient, said information being recorded by said second person on the apparatus in the form of predetermined encoded indicia; and
    a processor having at least one report section template corresponding to one of a patient's current medical condition, a patient's physical examination, a patient's diagnosis and a patient's treatment plan, said at least one report section template comprising optional text variable segments each of which are assigned to a selected one of said predetermined encoded indicia, said processor being operative to decode each of said one of the predetermined encoded indicia into its assigned optional text variable segment in said at least one discrete recording section and storing the same in a retrievable format.

3. The medical documentation system of claim 2 further comprising
    an imaging member responsive to the processor for preparing a patient's report specific to the designated patient's at least one of a medical condition, physical examination, diagnosis and treatment plan comprising the optional text variable segments stored in said retrievable format.

4. The medical documentation system of claim 3 wherein said processor includes
    a computer for the decoding each one of said predetermined encoded indicia into its corresponding optional text variable segment.

5. The medical history documentation system of claim 4 wherein said computer further comprises
    a comparator for comparing the optional text variable segment to the encoded indicia recorded on the recording member.

6. The medical history documentation system of claim 5 wherein said computer verifies the results of the comparison of the optional text variable segments with the encoded indicia.

7. A medical documentation system comprising:
   a recording member having a plurality of recording sections formed thereon for recording information relating to at least one of a designated patient's current medical condition, a physical examination, a diagnosis and a treatment plan;
   an input member for recording medical information communicated by a first person to a second person during a physical examination of the designated patient, said information being recorded by said second person in the recording member in the form of predetermined encoded indicia in at least one recording section of said recording member;
   a computer having a plurality of report section templates stored therein including a first report section template corresponding to a recording section for the patient's current medical condition, a second report section template corresponding to a recording section for the patient's physical examination, a third report section template corresponding to a recording section for the patient's diagnosis and a fourth report section template corresponding to a recording section for the patient's treatment plan, each of said report section templates comprising optional text variable segments each of which are assigned to a selected one of said predetermined encoded indicia;
   said computer being operative to decode each of said one of the predetermined encoded indicia recorded in the recording member into the assigned optional text variable segment in each applicable discrete recording section and storing the same in a retrievable memory location; and
   an imaging member responsive to the computer for preparing a patient's report specific to the designated patient's at least one of medical condition, physical examination, diagnosis and treatment plan comprising the optional text variable segments stored at retrievable memory locations.

8. The medical documentation system of claim 7 wherein said computer is programmable to assign an optional text variable segment to each one of said predetermined encoded indicia.

9. The medical documentation system of claim 7 wherein said computer further comprises
   a comparator for comparing the optional text variable segments to the encoded indicia recorded on the recording member.

10. The medical documentation system of claim 9 wherein said computer verifies the results of the comparison of the optional text variable segments with the encoded indicia recorded on the recording member.

11. The medical documentation system of claim 7 wherein the recording member is a form.

12. The medical history documentation of claim 11 wherein said form includes at least one discrete reporting section for recording information relating to a general examination of the designated patient.

13. The medical history documentation of claim 11 wherein said form includes at least one discrete reporting section for recording the information relating to a gynecology examination of the designated patient.

14. The medical history documentation of claim 11 wherein said form includes at least one discrete reporting section for recording information relating to an ophthalmologic examination of the designated patient.

15. The medical history documentation of claim 11 wherein said form includes at least one discrete reporting section for recording information relating to an urological examination of the designated patient.

16. The medical history documentation of claim 11 wherein said form includes at least one discrete reporting section for recording information relating to an orthopedic examination of the designated patient.

17. A medical history documentation system comprising:
   a recording member having a plurality of discrete recording sections formed thereon, each of said discrete recording sections being programmed to record information relating to at least one of a designated patient's current medical condition, a physical examination, a diagnosis and a treatment plan;
   an input member for recording medical information verbally communicated by a first person to a second person during a physical examination of the designated patient, said information being recorded on the recording member by said second person in the form of predetermined encoded indicia in at least one discrete recording section of said recording member;
   a transcriber for providing a plurality of report section templates including a first report section template corresponding to a discrete recording section for the patient's current medical condition, a second report section template corresponding to a discrete recording section for the patient's physical examination, a third report section template corresponding to a discrete recording section for the patient's diagnosis and a fourth report section template corresponding to a discrete recording section for the patient's treatment plan, each of said report section templates comprising a plurality of optional text variable segments each of which are assigned to a selected one of said predetermined encoded indicia, said transcriber being operative to decode each of said one of the predetermined encoded indicia recorded on said recording member into the optional text variable segment assigned thereto for each applicable discrete recording section; and
   an imaging device responsive to the transcriber for preparing a patient's report specific to the designated patient comprising a combination of selected optional text variable segments for a designated patient's at least one of medical condition, physical examination, diagnosis and treatment plan.

18. The medical history documentation system of claim 17 wherein said transcriber further comprises
   a computer which is includes a programming for the decoding of the optional text variable segments corresponding to each one of said predetermined encoded indicia.

19. The medical history documentation system of claim 18 wherein said computer further comprises
   a comparator for comparing the optional text variable segments to the encoded indicia recorded on the recording member.

20. The medical history documentation system of claim 19 wherein said computer verifies the results of the comparison of the optional text variable segments with the encoded indicia recorded on the recording member.

21. A method for documenting information for a designated condition comprising the steps of:
   conducting by a first person an examination of a designated condition in accordance with an examination procedure wherein the first person during the examination of the designated condition communicates first information of the condition to be documented;

recording by a second person on a recording device in a predetermined format said first information of the condition communicated by the first person during the examination of the designated condition resulting in recorded indicia;

processing said recorded indicia to produce in a programmable format a patient report containing the information of the designated condition; and comparing said patient report and said recorded indicia to verify the accuracy of the information.

22. A method for documenting verified patient medical information for a patient's history file comprising the steps of:

conducting by a first person a physical examination of a patient in accordance with an examination procedure wherein the first person during the physical examination of the patient communicates the patient medical information to be documented;

recording by a second person on a recording device in a predetermined encoded indicia format the patient medical information communicated by the first person during the physical examination of the patient;

processing said predetermined encoded indicia recorded by the recording device to produce in a programmable format a patient report containing the patient medical information; and comparing the patient medical information on the patient report with the patient medical information recorded by the recording device in said predetermined encoded indicia format to verify the accuracy of the patient medical information on the patient report.

23. The method of claim 22 further comprising the step of entering the verified patient report into a patient's history file.

24. The method of claim 22 wherein the step of comparing comprises the step of determining if the results of the comparison shows that the accuracy of the patient medical information is verified or unverified.

25. The method of claim 24 wherein the step of comparing further comprises the step of if the comparison of the determining step shows that the accuracy of the patient medical information is unverified, correcting the patient medical information to make the same verified.

26. The method of claim 22 wherein the step of recording by a first person comprises the step of writing the patient medical information on a preprinted form.

27. The method of claim 22 wherein the step of recording by a first person comprises the step of entering the patient medical information into a computer which is capable of performing the step of processing the medical information.

28. The method of claim 22 wherein the step of processing comprises dictating the patient medical information into a dictating system; and transcribing the dictation to produce the patient report.

29. The method of claim 22 wherein this step of processing comprises the step of programming the computer to process the patient medical information for producing an output signal representative of the patient report having the patient medical information.

30. The method of claim 29 wherein the step of processing further comprises generating in response to the output signal a display which represents the patient report.

31. The method of claim 29 wherein the step of comparing comprises electronically comparing the patient medical information as entered into the computer with the patient medical information contained in the output signal.

32. The method of claim 29 wherein the step of processing further comprises displaying the patient record containing the patient medical information as an image on a monitor in response to the output signal.

33. The method of claim 29 wherein the steps of processing further comprises the step of generating a patient report in the form of a printed image having the patient medical information.

* * * * *

(12) EX PARTE REEXAMINATION CERTIFICATE (7787th)
United States Patent
Shepard

(10) Number: US 5,704,371 C1
(45) Certificate Issued: Oct. 5, 2010

(54) MEDICAL HISTORY DOCUMENTATION SYSTEM AND METHOD

(75) Inventor: Franziska Shepard, Santa Maria, CA (US)

(73) Assignee: Magna Carta Holdings, LLC, Santa Maria, CA (US)

Reexamination Request:
No. 90/010,618, Jul. 27, 2009

Reexamination Certificate for:
Patent No.: 5,704,371
Issued: Jan. 6, 1998
Appl. No.: 08/611,642
Filed: Mar. 6, 1996

(51) Int. Cl.
*G06F 19/00* (2006.01)
*A61B 19/00* (2006.01)

(52) U.S. Cl. ..................... 128/897
(58) Field of Classification Search .......... None
See application file for complete search history.

(56) References Cited

U.S. PATENT DOCUMENTS

| 3,631,396 | A | 12/1971 | Spertus et al. |
| 5,065,315 | A | 11/1991 | Garcia |
| 5,197,487 | A | 3/1993 | Ackerman et al. |
| 5,704,371 | A | 1/1998 | Shepard |

OTHER PUBLICATIONS

Morris Simon, et al., Computerized Radiology Reporting Using Coded Language, Nov. 1974, pp. 343–350, vol. 113.

*Primary Examiner*—Matthew Heneghan

(57) ABSTRACT

A medical history documentation system and method for recording information relating to at least one of a designated patient's current medical condition, a physical examination, a diagnosis and a treatment plan is shown. The system includes a recording member having a plurality of discrete recording sections formed thereon programmed for recording information relating to the patient. The encoded indicia is communicated by a first person to a second person during a physical examination of the patient by the first person. An input member is used by the second person for recording medical information in the form of predetermined encoded indicia in applicable discrete recording sections of the recording member. A transcriber having a plurality of report section templates is used. Each report section template corresponds to a discrete recording section. Each of the report section templates comprise a plurality of optional text variable segments each of which are assigned to a selected one of the predetermined encoded indicia. The transcriber is operative to decode each one of the predetermined encoded indicia recorded on the recording member. An imaging device responsive to the transcriber prepares a patient's report specific to the designated patient. A method for using the system is shown.

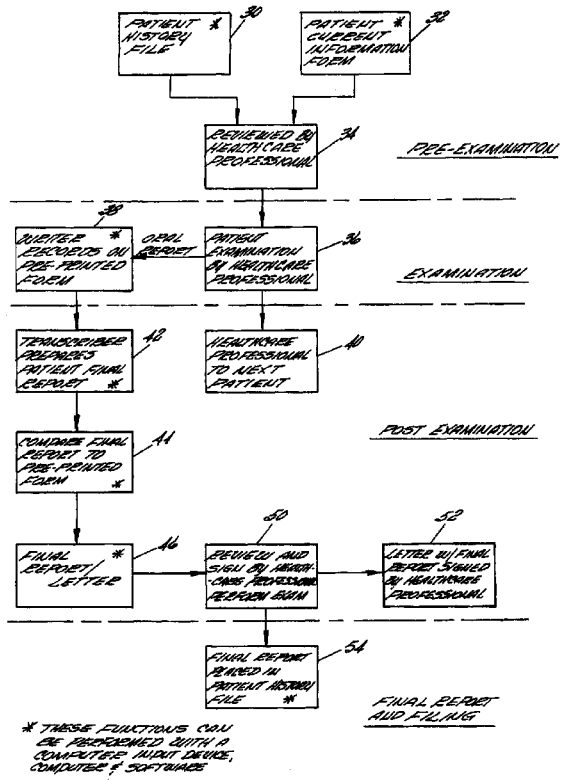

US 5,704,371 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 22-33 is confirmed.

Claims 1, 4, 5, 9, 18, 19 and 21 are cancelled.

Claims 2, 7 and 17 are determined to be patentable as amended.

Claims 3, 6, 8, 10-16 and 20, dependent on an amended claim, are determined to be patentable.

2. A medical documentation system comprising
apparatus for recording information relating to at least one of a designated patient's current medical condition, a physical examination, a diagnosis and a treatment plan;
an input device operative with said apparatus for recording medical information communicated by a first person to a second person during a physical examination of the designated patient, said information being recorded by said second person on the apparatus in the form of predetermined encoded indicia; and
a processor having at least one report section template corresponding to one of a patient's current medical condition, a patient's physical examination, a patient's diagnosis and a patient's treatment plan, said at least one report section template comprising optional text variable segments each of which are assigned to a selected one of said predetermined encoded indicia, said processor being operative to decode each of said one of the predetermined encoded indicia into its assigned optional text variable segment in said at least one discrete recording section and storing the same in a retrievable format, *said processor including a computer for the decoding each one of said predetermined encoded indicia into its corresponding optional text variable segment, wherein said processor includes a comparator for comparing the optional text variable segment to the encoded indicia recorded on the recording member.*

7. A medical documentation system comprising:
a recording member having a plurality of recording sections formed thereon for recording information relating to at least one of a designated patient's current medical condition, a physical examination, a diagnosis and a treatment plan;
an input member for recording medical information communicated by a first person to a second person during a physical examination of the designated patient, said information being recorded by said second person in the recording member in the form of predetermined encoded indicia in at least one recording section of said recording member;
a computer having a plurality of report section templates stored therein including a first report section template corresponding to a recording section for the patient's current medical condition, a second report section template corresponding to a recording section for the patient's physical examination, a third report section template corresponding to a recording section for the patient's diagnosis and a fourth report section template corresponding to a recording section for the patient's treatment plan, each of said section templates comprising optional text variable segments each of which are assigned to a selected one of said predetermined encoded indicia;
said computer being operative to decode each of said one of the predetermined encoded indicia recorded in the recording member into the assigned optional text variable segment in each applicable discrete recording section and storing the same in a retrievable memory location, *said computer including a comparator for comparing the optional text variable segments to the encoded indicia recorded on the recording member*; and
an imaging member responsive to the computer for preparing a patient's report specific to the designated patient's at least one of medical condition, physical examination, diagnosis and treatment plan comprising the optional text variable segments stored at retrievable memory locations.

17. A medical history documentation system comprising:
a recording member having a plurality of discrete recording sections formed thereon, each of said discrete recording sections being programmed to record information relating to at least one of a designated patient's current medical condition, a physical examination, a diagnosis and a treatment plan;
an input member for recording medical information verbally communicated by a first person to a second person during a physical examination of the designated patient, said information being recorded on the recording member by said second person in the form of predetermined encoded indicia in at least one discrete recording section of said recording member;
a transcriber for providing a plurality of report section templates including a first report section template corresponding to a discrete recording section for the patient's current medical condition, a second report section template corresponding to a discrete recording section for the patient's physical examination, a third report section template corresponding to a discrete recording section for the patient's diagnosis and a fourth report section template corresponding to a discrete recording section for the patient's treatment plan, each of said report section templates comprising a plurality of optional text variable segments each of which are assigned to a selected one of said predetermined encoded indicia, said transcriber being operative to decode each of said one of the predetermined encoded indicia recorded on said recording member into the optional text variable segment assigned thereto for each applicable discrete recording section; [and]
an imaging device responsive to the transcriber for preparing a patient's report specific to the designated patient comprising a combination of selected optional text variable segments for a designated patient's at least one of medical condition, physical examination, diagnosis and treatment plan; *and* a computer which is includes a programming for the decoding of the optional text variable segments corresponding to each one of said predetermined encoded indicia, the computer including a comparator for comparing the optional text variable segments to the encoded indicia recorded on the recording member.

\* \* \* \* \*